(12) United States Patent
Machida et al.

(10) Patent No.: US 7,194,121 B2
(45) Date of Patent: *Mar. 20, 2007

(54) METHOD OF MEASURING A BIOMAGNETIC FIELD, METHOD OF ANALYZING A MEASURED BIOMAGNETIC FIELD, METHOD OF DISPLAYING BIOMAGNETIC FIELD DATA, AND AN APPARATUS THEREFOR

(75) Inventors: Kazuhisa Machida, Kawasaki (JP); Takafumi Kawasaki, Sagamihara (JP); Hiroyuki Suzuki, Hitachinaka (JP); Keiji Tsukada, Kashiwa (JP)

(73) Assignee: Hitachi, Ltd., Tokyo (JP)

( * ) Notice: Subject to any disclaimer, the term of this patent is extended or adjusted under 35 U.S.C. 154(b) by 336 days.

This patent is subject to a terminal disclaimer.

(21) Appl. No.: 10/770,525

(22) Filed: Feb. 4, 2004

(65) Prior Publication Data

US 2004/0158168 A1    Aug. 12, 2004

Related U.S. Application Data

(63) Continuation of application No. 10/282,158, filed on Oct. 29, 2002, now Pat. No. 6,711,281, which is a continuation of application No. 09/164,271, filed on Oct. 1, 1998, now Pat. No. 6,473,518.

(30) Foreign Application Priority Data

Oct. 2, 1997   (JP) .................................... 9-270157
Oct. 2, 1997   (JP) .................................... 9-270158

(51) Int. Cl.
   *G06K 9/00*   (2006.01)
   *G06K 9/20*   (2006.01)

(52) U.S. Cl. ...................................... 382/128; 382/320

(58) Field of Classification Search ................ 382/128, 382/320; 600/409; 324/248
See application file for complete search history.

(56) References Cited

U.S. PATENT DOCUMENTS

| | | | |
|---|---|---|---|
| 4,771,239 A | 9/1988 | Hoenig | 324/248 |
| 4,974,602 A | 12/1990 | Abraham-Fuchs et al. | 128/731 |

(Continued)

FOREIGN PATENT DOCUMENTS

JP    2-40578    2/1990

(Continued)

*Primary Examiner*—Duy M. Dang
(74) *Attorney, Agent, or Firm*—Antonelli, Terry, Stout and Kraus, LLP.

(57) ABSTRACT

A biomagnetic field map display apparatus for measuring a biomagnetic field generated by a biotest sample at positions arranged in rows and columns and displaying a magnetic field map obtained by processing the measured biomagnetic field. An analysis data display area waveform-displays the measured biomagnetic field at channels in a row or a column of channels which are arranged in rows and columns so as to respectively correspond to the positions. A particular channel is designated as a reference channel for an averaging process out of the plurality of channels or different channels therefrom at which different biosignals from those of the biomagnetic field are acquired from the biotest sample. Means for averaging-processing the measured biomagnetic field using the designated particular channel as the reference channel displays in the analysis data display area a map on the averaging-processed biomagnetic field.

2 Claims, 28 Drawing Sheets

U.S. PATENT DOCUMENTS

| | | | |
|---|---|---|---|
| 5,047,754 A | 9/1991 | Akatsuka et al. | 340/709 |
| 5,285,385 A | 2/1994 | Igarashi et al. | 600/409 |
| 5,299,138 A | 3/1994 | Fiori et al. | 702/22 |
| 5,427,113 A | 6/1995 | Hiroshi et al. | 128/734 |
| 5,563,962 A | 10/1996 | Peters et al. | 382/261 |
| 5,594,849 A | 1/1997 | Kuc et al. | 395/135 |
| 5,964,719 A | 10/1999 | Costello et al. | 600/595 |
| 6,059,718 A | 5/2000 | Taniguchi et al. | 600/117 |
| 6,230,037 B1 | 5/2001 | Tsukada et al. | 600/409 |
| 6,275,719 B1 | 8/2001 | Kandori et al. | 600/409 |
| 6,336,043 B1 | 1/2002 | Suzuki et al. | 600/409 |
| 6,373,970 B1 | 4/2002 | Dong et al. | 382/128 |
| 6,473,518 B1 * | 10/2002 | Machida et al. | 382/128 |
| 6,477,398 B1 | 11/2002 | Mills | 600/409 |
| 6,711,281 B2 * | 3/2004 | Machida et al. | 382/128 |
| 2002/0054697 A1 | 5/2002 | Wang | 382/128 |
| 2003/0097056 A1 | 5/2003 | Suzuki et al. | 600/409 |

FOREIGN PATENT DOCUMENTS

| | | |
|---|---|---|
| JP | 02-268741 | 11/1990 |
| JP | 03-272736 | 12/1991 |
| JP | 4-35643 | 2/1992 |
| JP | 4-93782 | 3/1992 |
| JP | 04-141140 | 5/1992 |
| JP | 4-319334 | 11/1992 |
| JP | 04-348476 | 12/1992 |
| JP | 5-146416 | 6/1993 |
| JP | 6-114022 | 4/1994 |
| JP | 6-237917 | 8/1994 |
| JP | 7-184871 | 7/1995 |
| JP | 07-194600 | 8/1995 |
| JP | 8-266499 | 10/1996 |
| JP | 09-173313 | 7/1997 |
| JP | 10-295661 | 11/1998 |
| JP | 11-4814 | 1/1999 |
| JP | 11-4815 | 1/1999 |
| JP | 11-104095 | 4/1999 |

* cited by examiner

FIG. 10

Patient Registration

Registration Date:

ID:
Name:
DOB:
Height:
Weight:
Class:
Sex: ● Male ○ Female
Comment:

[OK] [CANCEL] [CLOSE]

FIG. 11

Reg. Date:
ID:
Family Name:
First Name:
DOB:    Age:
Height: Class:
Weight:
Sex:

Type of Data:
DACQ. Date:
Result of Diagnosis:
Inspected by:

[OK] [CANCEL]

FIG. 12

| Manual Adjustment | | | |
|---|---|---|---|
| Channel | Ibias | Voff | |

OK

CANCEL

FIG. 13

Sensor Diagnosis

☒ Min. Amplitude
☒ Center
☒ Period

OK    CANCEL

FIG. 24

| ID | Name | Registration | DACQ | DOB | Age | Height | Weight | Class | Comment |
|---|---|---|---|---|---|---|---|---|---|
| 00000000000000 | Hiroyuki,Suzuki | 1997/07/01 | 3 | 1959/10/01 | 37 | 180.0cm | 80.0Kg | Normal | |

| ID | Raw Data ID | Interval | Sampling Points | Addition Counts | Sampling Date | Time | Base Line |
|---|---|---|---|---|---|---|---|
| 001 | 001 | 0.5 msec | 2000 | 100 | 1997/08/15 | 12:05:00 | Corrected |
| 002 | 001 | 0.5 msec | 2000 | 100 | 1997/08/15 | 13:05:00 | Corrected |
| 003 | 001 | 0.5 msec | 2000 | 10 | 1997/08/15 | 13:15:00 | |

METHOD OF MEASURING A BIOMAGNETIC FIELD, METHOD OF ANALYZING A MEASURED BIOMAGNETIC FIELD, METHOD OF DISPLAYING BIOMAGNETIC FIELD DATA, AND AN APPARATUS THEREFOR

CROSS-REFERENCE TO RELATED APPLICATIONS

This is a continuation of U.S. application Ser. No. 10/282,158 filed 29 Oct. 2002, now U.S. Pat. No. 6,711,281, which is a continuation of U.S. application Ser. No. 09/164,271 filed 1 Oct. 1998, now U.S. Pat. No. 6,473,518 B1.

BACKGROUND OF THE INVENTION

1. Field of the Invention

The present invention relates to techniques for measuring a biomagnetic field, analyzing a measured biomagnetic field and displaying biomagnetic field data.

2. Description of the Prior Art

There is known a prior art multi-channel bio magnetic field imaging system which uses a magnetic sensor of superconducting quantum interference device (SQUID) in order to measure a weak magnetic field generated in the human body, estimates the positions of the sources of its bio current from the result of measurement, and obtains its distribution as an image. Such prior arts are disclosed, for example, in JPA-4-319334 and 5-146416.

These prior arts are concerned with principles of operation of the bio-magnetic imaging systems, and do not describe any particular technical problems to be solved or its specific method suitable for practice. Further, the above-mentioned prior arts are related to the bio-activity currents generated in the brain, and do not disclose such bio-active currents in other parts of the body.

SUMMARY OF THE INVENTION

An object of the invention is to provide a method of measuring a biomagnetic field, a method of analyzing a measured biomagnetic field, and a method of displaying biomagnetic field data and an apparatus therefor, which are easy to manage and operate.

Another object of the invention is to provide a method of and an apparatus for displaying biomagnetic field data obtained at a plurality of positions of a biotest sample in an improved easy-to-observe way.

According to one aspect of the invention, a method is provided for measuring a magnetic field emitted from a biotest sample or analyzing a measured magnetic field, which comprises a step of performing a first display indicative of a first function including operation to register a new biotest sample or a second display indicative of a second function to display a list of biotest samples, wherein by selecting the first display, biotest sample input items are displayed through which data relating to the biotest sample are entered and registered, and by selecting the second display, the list of biotest samples registered is displayed.

According to another aspect of the invention, a method of measuring a magnetic field emitted from a biotest sample at a plurality of positions is provided, which comprises the steps of: displaying said plurality of positions on a screen; selecting any of said plurality of positions; displaying information regarding a magnetic field strength at the selected position; and displaying said plurality of positions and whether said plurality of positions are selected or not on the screen, with said information regarding the magnetic field strength being displayed.

According to still another aspect of the invention, a biomagnetic field data display device for displaying a magnetic field data obtained by measuring a biomagnetic field emitted from a biotest sample at a plurality of positions is provided, which comprises: a process function display area showing process function items; an analysis data display area which displays the measured biomagnetic field and a processed magnetic field thereof; and an operating region display area, wherein said operating region display area displays respective operating items corresponding to said measured magnetic field data and said processed magnetic field data, wherein contents of display in said operating region display area are changeable by selection of a corresponding item in said process function display area, and wherein said process function display, said analysis data display and said operating item display are displayed on the same screen.

According to still more aspect of the invention, a biomagnetic field data display device for displaying magnetic field data obtained from a biomagnetic field emitted from a biotest sample and measured at a plurality of positions thereof on a screen is provided, wherein said screen comprises: a process function display area showing process function items, disposed in an upper portion of the screen; a test sample information display area for showing information relating to a test sample, disposed in a left side portion of the screen; an analysis data display area, disposed in a center portion of the screen; and an operating region display area including a channel display area for displaying channels corresponding to said plurality of positions and for selecting any of said channels, disposed in a right side portions of the screen.

According to still another aspect of the invention, a biomagnetic field data display method for displaying magnetic field data obtained from biomagnetic fields emitted from a biotest sample measured at a plurality of positions thereof is provided, which comprises the steps of: instructing to display a biotest sample list screen from a process function item in a process function display area; selecting a measurement item in said process function display area to display an analysis data display area for displaying biomagnetic field data and an operating region display area through which the contents of display in said analysis data display area can be switched; displaying a grid map in said analysis data display area as its initial screen; displaying a progress bar indicative of a state of progress of measurement operation; and upon completion of measurement, displaying biomagnetic field data or its processed magnetic field data on the analysis data display area.

The above-mentioned and other objects and features of the invention will become apparent from the following description of embodiments with reference to the accompanying drawings.

BRIEF DESCRIPTION OF THE DRAWINGS

FIG. 10 is a diagram showing the contents of a patient registration dialog frame which is opened when "List (L)-Registration (R)" are selected as operation menu in the displayed on the display section in the biomagnetic instrument of FIG. 1;

FIG. 11 is a diagram showing the contents of a search dialog frame which is opened when "List (L)-Search (S)" is selected as operation menu in the displayed on the display section in the biomagnetic instrument of FIG. 1;

FIG. 12 shows the contents of a manual adjustment dialog frame which is opened when "Measurement (Q)-Manual adjustment (M)" is selected as its operation menu in the displayed on the display section in the biomagnetic instrument of FIG. 1;

FIG. 13 shows the contents of an automatic diagnosis dialog frame which is opened when "Measurement (Q)-Measurement Panel (P)" is selected as it operation menu in the displayed on the display section in the biomagnetic instrument of FIG. 1;

FIG. 24 shows a patient list screen displayed on the display section of the biomagnetic instrument of FIG. 1;

DETAILED DESCRIPTION OF THE INVENTION

Figure 1:
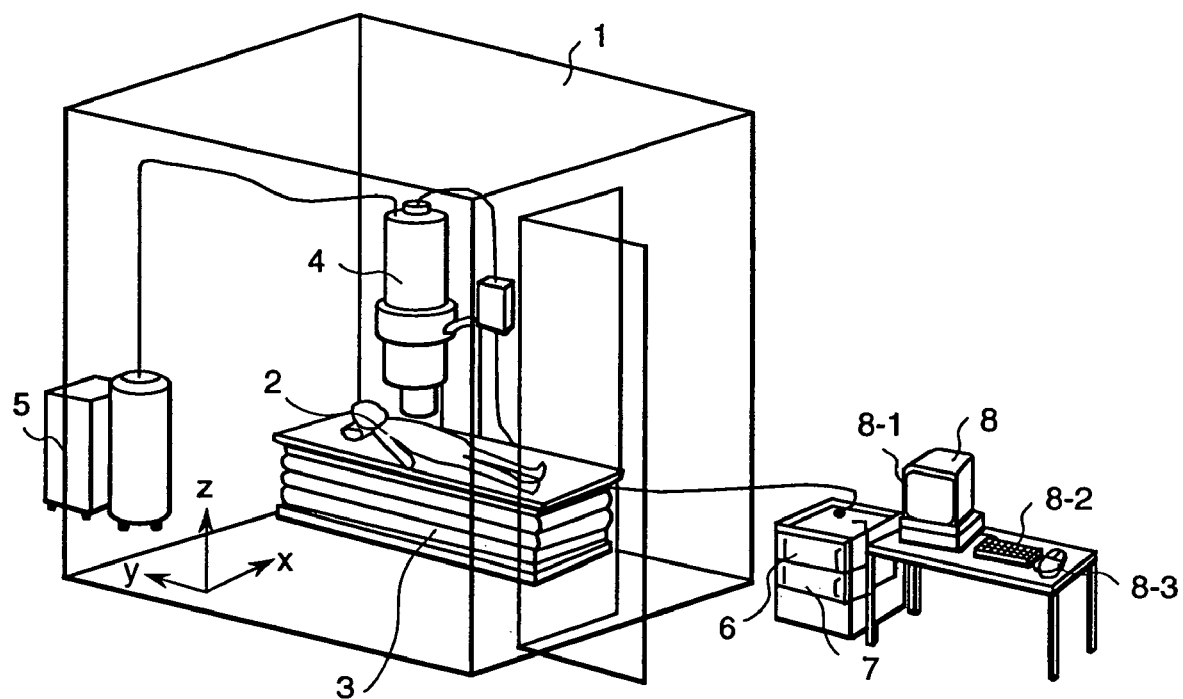
FIG. 1 is a schematic diagram of a biomagnetic instrument of one embodiment of the invention.

FIG. 1 is a schematic block diagram indicative of a biomagnetic instrument of one embodiment of the invention. In order to eliminate any influence of environmental magnetic noise, the biomagnetic instrument is installed in a magnetic shield room 1. A patient 2 to be tested lies on a bed 3 on his/her back for measurement thereof. A body plane of the patient (a plane parallel to the chest-wall, in case of a chest portion) is assumed to be approximately parallel with the plane of bed 3, and this parallel plane is assumed to be parallel with an x-y plane of an orthogonal system (x, y, z). Although an actual chest portion of the patient is curved and slanted, it is assumed to be substantially parallel in order to simplify the description.

In the upper direction of the chest part of patient 2, there is disposed a dewar 4 filled with a coolant of liquid helium (He). This dewar 4 accommodates superconducting quantum interference devices (SQUID) and a plurality of magnetic sensors including detection coils connected to this SQUID. The liquid He is supplied continuously from an automatic He supplier 5 provided outside the magnetic shield 1.

The magnetic sensor produces a voltage which has a specific relation with a biomagnetic field strength (or biomagnetic flux density) which is generated in the patient 2 and detected by the detection coils. This output voltage is input to a flux locked loop (FLL) circuit 6. In order to ensure for the output of SQUID to be maintained constant, this FLL circuit 6 cancels changes in the biomagnetic fields (biomagnetism) input into SQUID by means of a feedback coil, which is referred to as a magnetic flux lock. By conversion of this feedback current flowing through the feedback coil to a voltage, a voltage output that has a specific relationship with the changes in biomagnetism signals can be obtained. By provision of such a detection method by means of the feedback coil as described above, a very weak magnetic field can be detected at a high precision.

The above-mentioned output voltage is entered into an amplifier/filter/amplifier (AFA) unit 7, and their outputs are sampled, subjected to A/D conversion, then entered to a computer 8.

Computer 8 is comprised of a personal computer, and numeral 8-1 depicts its display unit, 8-2 depicts its keyboard, and 8-3 depicts its mouse. The mouse is used for moving a cursor on a panel or screen to select an object to be processed. This operation can be executed also by operation of the keyboard. Further, an input gain 1 and an output gain 0 of AFA 7 are adjustable, and AFA 7 includes: a low-pass filter (LPF) which allows to pass a frequency signal which is lower than a first reference frequency; a high-pass filter (HPF) which allows to pass a frequency signal which is lower than the first reference frequency and higher than a second reference frequency; and a band elimination filter (BEF) which cuts off the commercial power line frequency. Computer 8 can execute various data processing, and a result of its processing can be displayed on display unit 8-1. The above-mentioned computer 8 depicted in FIG. 1 shows only one embodiment of the invention, and it is not limited thereto. There can be considered in the scope of the invention various modifications such as ones having a display provided with a touch panel, a coordinate indicator in place of the mouse, for example, using a track ball, joystick or the like as well. Further, a mobile computer that can be coupled via the public telephone circuitry may be used.

For example, a direct current SQUID is used as the SQUID of the invention. A direct bias current Ibias is applied to flow through SQUID such that when an external magnetic field is applied to the SQUID, a voltage V corresponding to the applied external magnetic field is produced. Assuming this applied external magnetic field to be expressed by magnetic flux $\phi$, a characteristic curve of V relative to $\phi$, i.e., characteristic curve $\phi$-V, is given by a periodic function. Prior to measurement, operation to set a DC voltage of the $\phi$-V characteristic curve at 0 level is carried out by adjusting the offset voltage Voff of FLL circuit 6. Further, operation to adjust the offset voltage Aoff of AFA 7 is carried out such that the output of AFA 7 becomes 0 when its input is zero.

When the external magnetic field applied to SQUID becomes substantially great, this magnetic field tends to be trapped in the SQUID, thereby preventing normal operation from being ensured. In such a case, SQUID is heated once and returned to its normal conducting state so as to remove the trapped magnetic field. This procedure of heating the SQUID will be referred to as the heat flash hereinafter.

Figure 2:
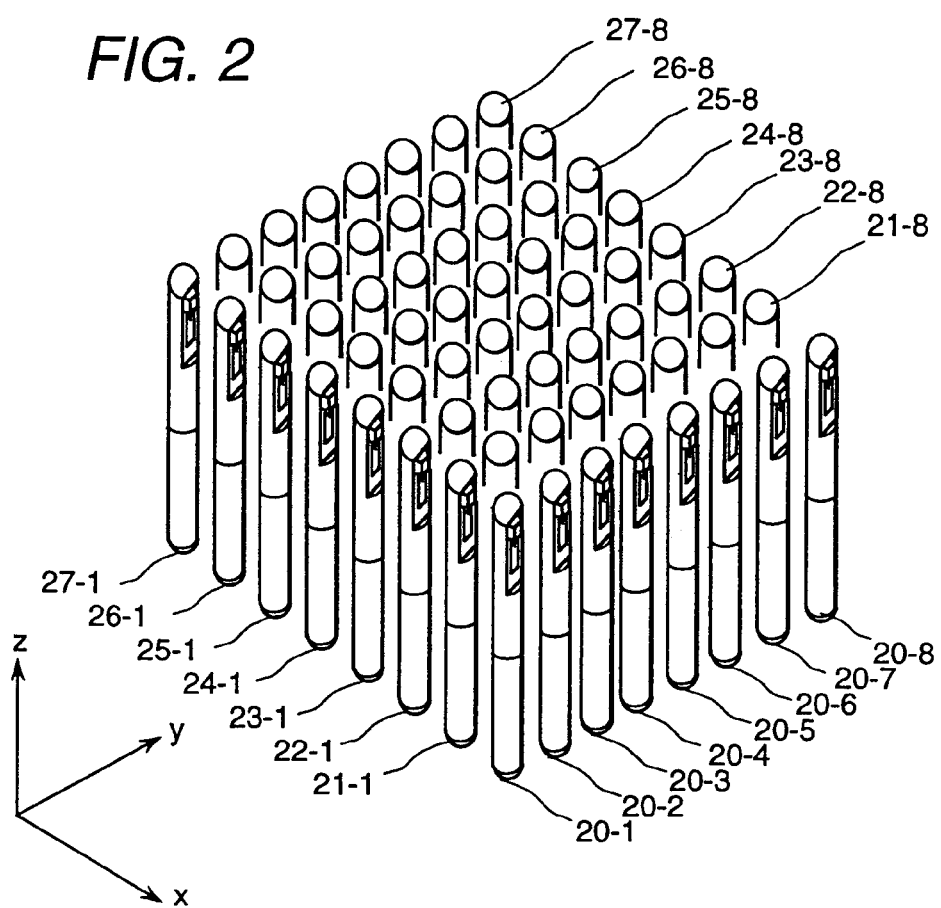
FIG. 2 is a perspective view of the arrangement of a magnetic sensor for use in the biomagnetic instrument of FIG. 1.

FIG. 2 shows a layout of magnetic sensors of the invention. The detection coil of each magnetic sensor has two types of coils: one for detecting tangential components of the biomagnetic field (components substantially parallel to the body of the patient, i.e., x-y plane); and the other for detecting normal components of the biomagnetic field (components perpendicular to the body plane, or x-y plane). As the coil for detecting the tangential components of the biomagnetic field, two different coils, one with its coil plane disposed in x direction and the other disposed in y direction are used. As the coil for detecting the normal components of the biomagnetic field, a coil with its coil plane disposed in z direction is used. A plurality of magnetic sensors from 20-1 to 20-8, from 21-1 to 21-8, from 22-1 to 22-8, from 23-1 to 23-8, from 24-1 to 24-8, from 25-1 to 25-8, from 26-1 to 26-8, and from 27-1 to 27-8 are disposed in a matrix on a plane which is substantially parallel to the patient body, i.e., x-y plane. The number of the magnetic sensors may be any number. In FIG. 2, however, because the matrix is comprised of 8 rows by 8 columns, the number of magnetic sensors therein is 8×8=64. Each magnetic sensor is disposed such that its longitudinal direction becomes perpendicular (in the z direction) to the patient body, or to the x-y plane. By way of example, although the bed surface and the x-y plane of the sensors are depicted to be parallel to each other in this embodiment of the invention, it is not limited thereto, and they can be slanted because it is more preferable to allow for these two planes to come into a close proximity in order to improve precision of detection. However, since the human body of the patient is always in motion, if the sensors are placed in direct contact with the human body, this motion will cause to move the detectors thereby preventing a high precision detection from being obtained.

Figure 3:
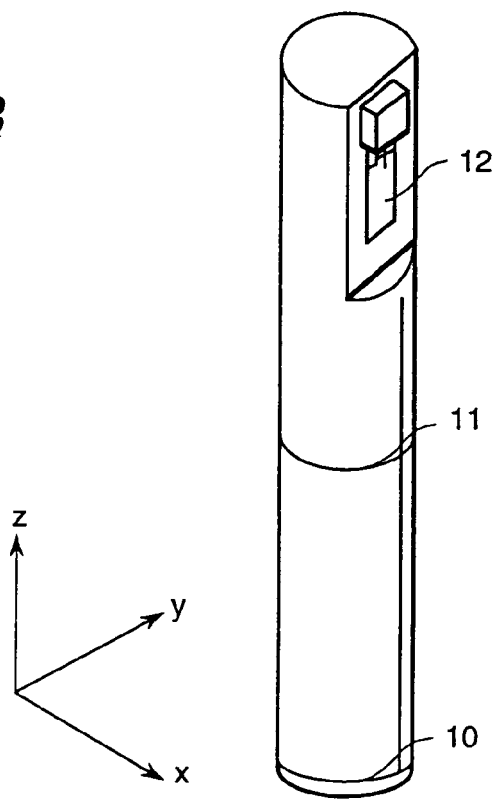
FIG. 3 is a perspective view of a unit of magnetic sensor for use in the biomagnetic instrument of FIG. 1 and for detection of a normal component of the magnetic field.

FIG. 3 shows the structure of a sensor in each magnetic sensor for use in detection of normal component Bz of the biomagnetic field. The coil of this sensor which is made of an Ni—Ti superconducting wire is disposed such that its coil plane becomes perpendicular to the z-direction. This coil is comprised of a combination of two reverse-wound coils 10 and 11, and its coil 10 which is closer to the patient 2 functions as a detection coil, and the other coil 11 remote from the patient serves as a reference coil, which detects external magnetic field noise. The external magnetic field noise comes from an external signal source which is more remote than the patient. Therefore, this noise signal can be detected by both the detection coil 10 and the reference coil 11. On the other hand, because a biomagnetic signal from the patient is weak, this weak biomagnetic signal is detected only by the detection coil 10, and the reference coil 11 is almost insensitive to this biomagnetic signal. Therefore, because the detection coil 10 is allowed to detect both the biomagnetic signal and the external magnetic noise signal while the reference coil 11 is allowed to detect only the external magnetic noise signal, it becomes possible to obtain a high precision biomagnetic field data with an improved S/N ratio by taking a difference (subtraction) between these two signals obtained by these two coils. These coils are connected to an input coil of SQUID via a superconducting wire of a packaged substrate on which SQUID 12 is mounted, whereby normal direction component Bz of the detected biomagnetic signal is transmitted to SQUID.

Figure 4:
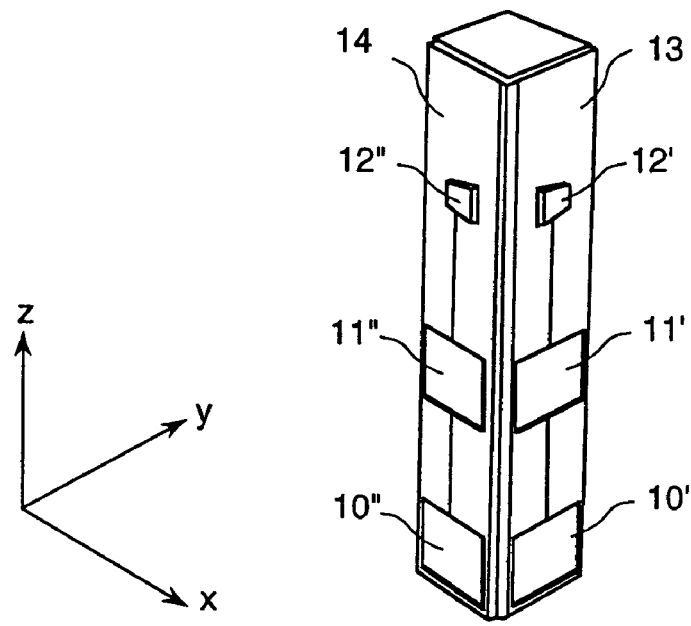
FIG. 4 is a perspective view of a unit of magnetic sensor of another embodiment for use in the biomagnetic instrument of FIG. 1 for detecting a tangential component of the magnetic field.

FIG. 4 shows arrangements of respective sensors of each magnetic sensor for detecting tangential components Bx and By of the biomagnetic field. In the same drawing, the respective sensors for use in the detection of biomagnetic field components in the tangential directions utilize a planar coil. That is, its detection coils 10' and 10", and its reference coils 11' and 11" are comprised of planar coils, and they are disposed on a first and a second surfaces respectively which are separated from each other at a given distance in the z-directions. Further, in the same manner as in the normal components' coil connection, these coils are connected to the input coils of package substrates of SQUID 12' and SQUID 12", respectively. A sensor 13 for use in the detection of Bx component and a sensor 14 for use in the detection of By component are attached on two adjacent and perpendicular surfaces of a rectangular pole, whereby a sensor capable of detecting Bx component as well as By component is provided.

As for the tangential components Bx and By, they can be obtained, without using the magnetic sensors depicted in FIG. 4, through partial differentials of the normal component Bz with respect to x and y, which was obtained using the magnetic sensor of FIG. 3. In this case, using one magnetic sensor, tangential components Bx and By as well as normal component Bz can be detected for their measurement.

Figure 5:
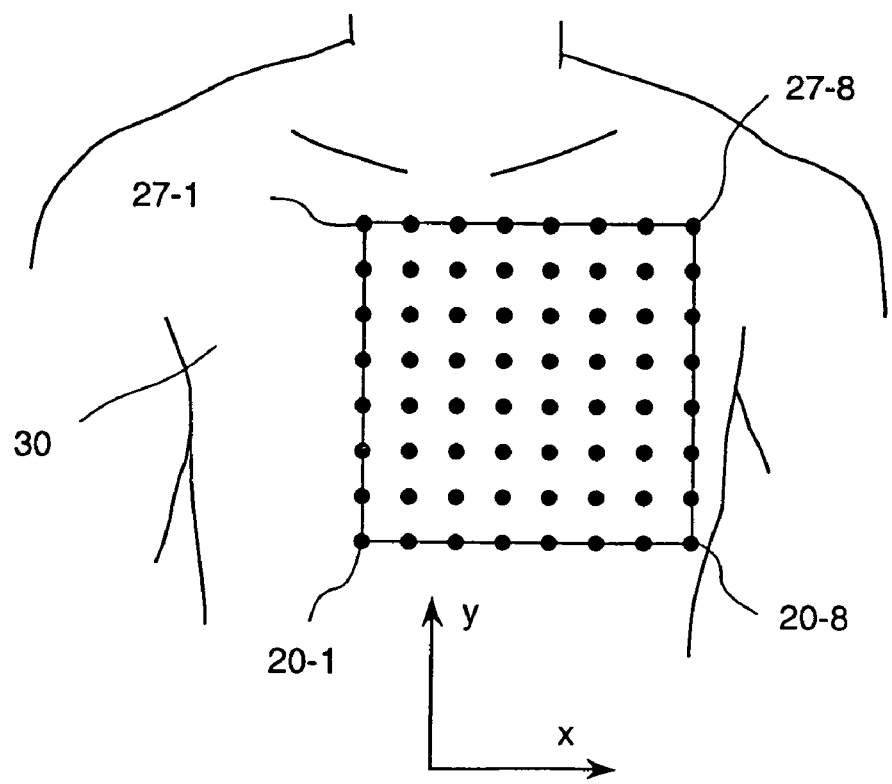
FIG. 5 is a diagram indicating a positional relationship between the magnetic sensors of the biomagnetic instrument of FIG. 1 and the chest portion of a patient.

FIG. 5 shows a positional relationship between the magnetic sensors and chest portion 30 of the patient 2 under detection. Respective dots shown in the drawing represent intersections between the rows and columns in the matrix of FIG. 2, namely, respective points of measurement on the patient 2, or positions of detection. These positions of detection may be referred to as channels. As obviously indicated in this embodiment, the direction of height of the patient 2 coincides with y-direction, and the direction of width of the patient coincides with x-direction.

Figure 6A:
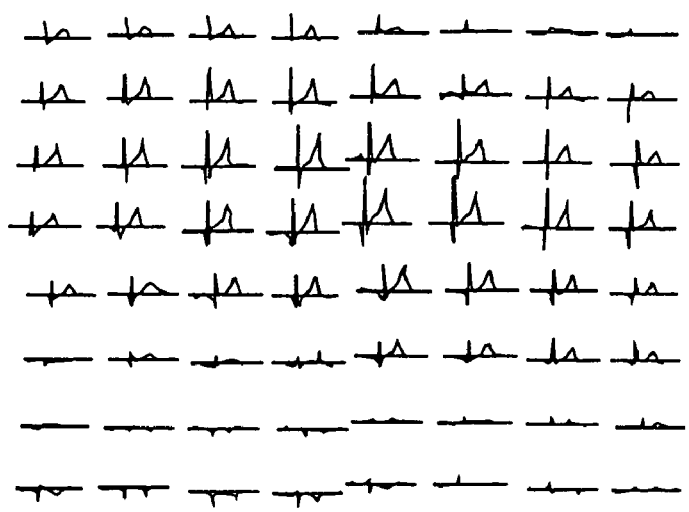
FIGS. 6(A)–(C) are time waveform diagrams of respective components of biomagnetic fields (cardiomagnetic waveforms) measured for a healthy person by respective magnetic sensors in the biomagnetic instrument.
Figure 6B:
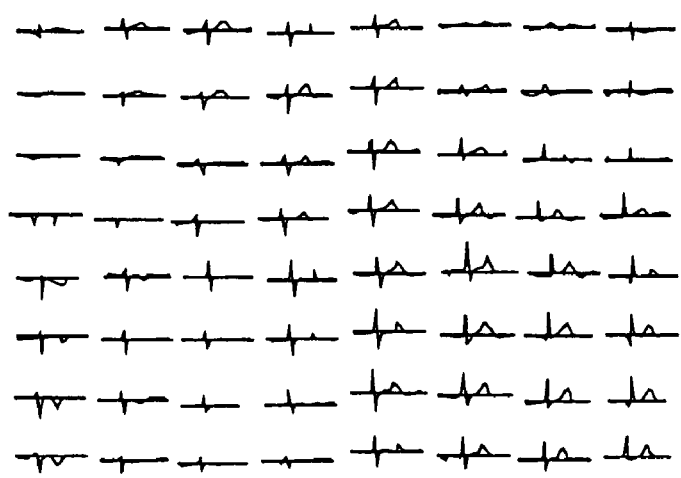
Figure 6C:
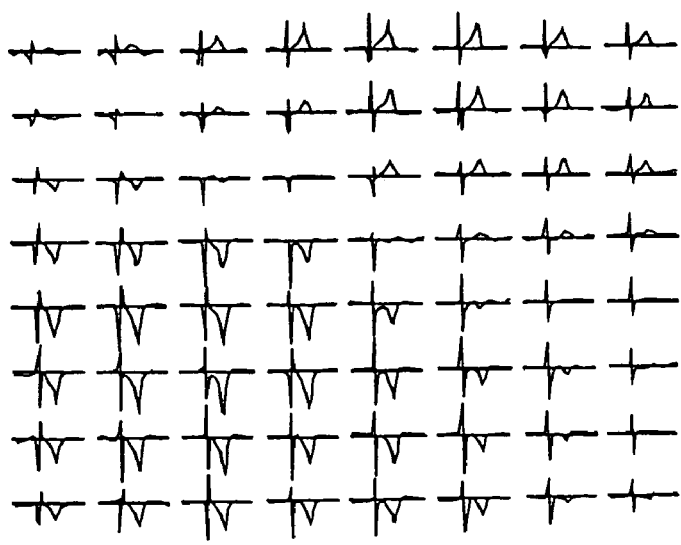

FIGS. 6(A)–(C) show the results of measurement at respective measurement positions (channels) of FIG. 5. This result of measurement shows respective biomagnetic field waves changing with time at respective corresponding channels in the matrix which were obtained through the above-mentioned data processing of respective signals detected by respective magnetic sensors corresponding to their measurement positions. The waveforms in FIG. 6 depict the cardiomagnetic waveforms of the patient because respective channels are placed at respective positions capable of detecting biomagnetic fields produced by myocardia in this embodiment of the invention. By way of example, the waveform obtained by detection of the biomagnetic fields produced by myocardial activities is referred to as the cardiomagnetic waveform. In the case where the result of measurement at each channel of detection is displayed in a matrix corresponding to its position as shown in FIG. 6, this display will be referred to as a grid map imaging. FIGS. 6(A)–(C) show the cardiomagnetic waveforms obtained for a healthy person. FIG. 6(A) depicts cardiomagnetic waveforms of tangential components Bx, FIG. 6(B) depicts that of tangential components By, and FIG. 6(C) depicts that of normal components Bz, respectively.

Figure 7:
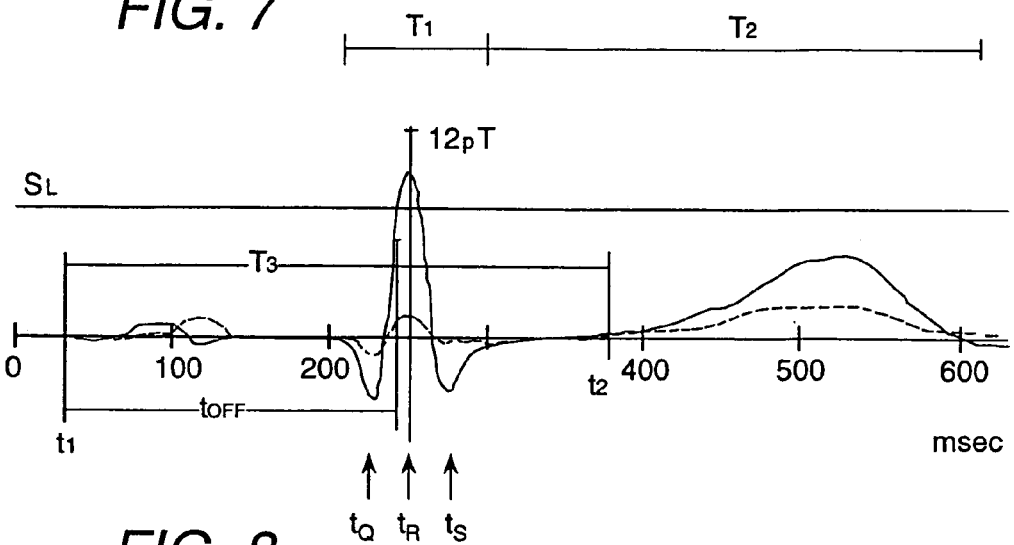
FIG. 7 is a diagram indicating tangential components of cardiomagnetic time waveforms at two channels specified and measured for a healthy person using the biomagnetic instrument of the FIG. 1.

FIG. 7 shows cardiomagnetic waveforms of tangential component Bx obtained for a healthy person and, in particular, with respect to designated two channels. A solid line depicts a cardiomagnetic waveform of one of these two channels and a dotted line depicts that of the other channel thereof. Respective waveforms in time span T1 undergoing de-polarization of the ventricle of the heart, namely, QRS waves in the contraction period thereof are shown having respective peak times for their waveforms at tQ, tR and tS. Further, a time span of T wave corresponding to the re-polarization process (expansion period) of the heart is indicated as T2. In addition to the grid map display, the results of measurement may be displayed also by a single channel data display method which displays a single channel data per each row or each column, otherwise by a multiple channel data display method which displays by superimposing every channel data or a plurality of selected channel data. The former is referred to as the single waveform display, and the latter is referred to as the multichannel wave display.

The cardiomagnetic waveform data, or more generally, measured biomagnetic field data obtained as above are subjected to averaging processing, contour mapping of magnetic flux and that of time integral thereof, and the results of such processing can be displayed. For example, in reference to FIG. 7, a predetermined time (toff) is retrospected from a time at which a raising part of QRS wave intersects a threshold line SL to a time t1, then data occurring within a time slit T3 between time t1 and time t2 are added for a predetermined count. This is the averaging operation, and the predetermined time slit T3 is its averaging period of time, and the predetermined time slit toff is its off-set time. The cardiomagnetic wave data may be obtained also by integrating it over a predetermined time span. A contour map obtained by connecting equal points (channels) of such time integral is referred to as the contour map of time integral. Further, a contour map obtained by connecting equal points (channels) of cardiomagnetic wave signals is referred to as the contour map of magnetic flux. Further, although respective channels are set up coarsely, a pitch between contours of mapping, namely, a difference between magnetic field strengths may be predetermined appropriately, then by linearly interpolating between these respective channels, contour mapping of magnetic flux can be drawn suitable for more precise diagnosis. As for the cardiomagnetic waves indicated in FIG. 7, a period of time from time t1 to time tR which coincides with the peak point of QRS wave is called as a propagation time, and a map obtained by connecting equal points of its propagation time is called as a contour map of propagation time. A set level of the threshold line SL is changeable. As for time t1 which is determined on the basis of the time at which the rising part of QRS wave intersects the threshold line SL, it may be determined on the basis of a time at which its falling part of QRS wave intersects the threshold line SL. Still further, the time t1 may be determined, by detecting time tR corresponding to a peak point of the QRS wave, and with reference to this detected time tR. A biomagnetic signal obtained according to the invention is produced by bioelectronic phenomena in the human body, and the source of its signal can be approximated by a current dipole model. The current dipole model approximated as the source of its biomagnetic field is synthesized on the contour map of magnetic flux and displayed thereon, which is referred to as a magnetic source imaging.

A series of operation including the registration of the patient, measurement on the patient registered, and its data analysis are executed while monitoring the screen or panel displayed on display unit 8-1. Therefore, at first, layouts of these screens will be described prior to detailed descriptions of these series of operation.

Figure 8:
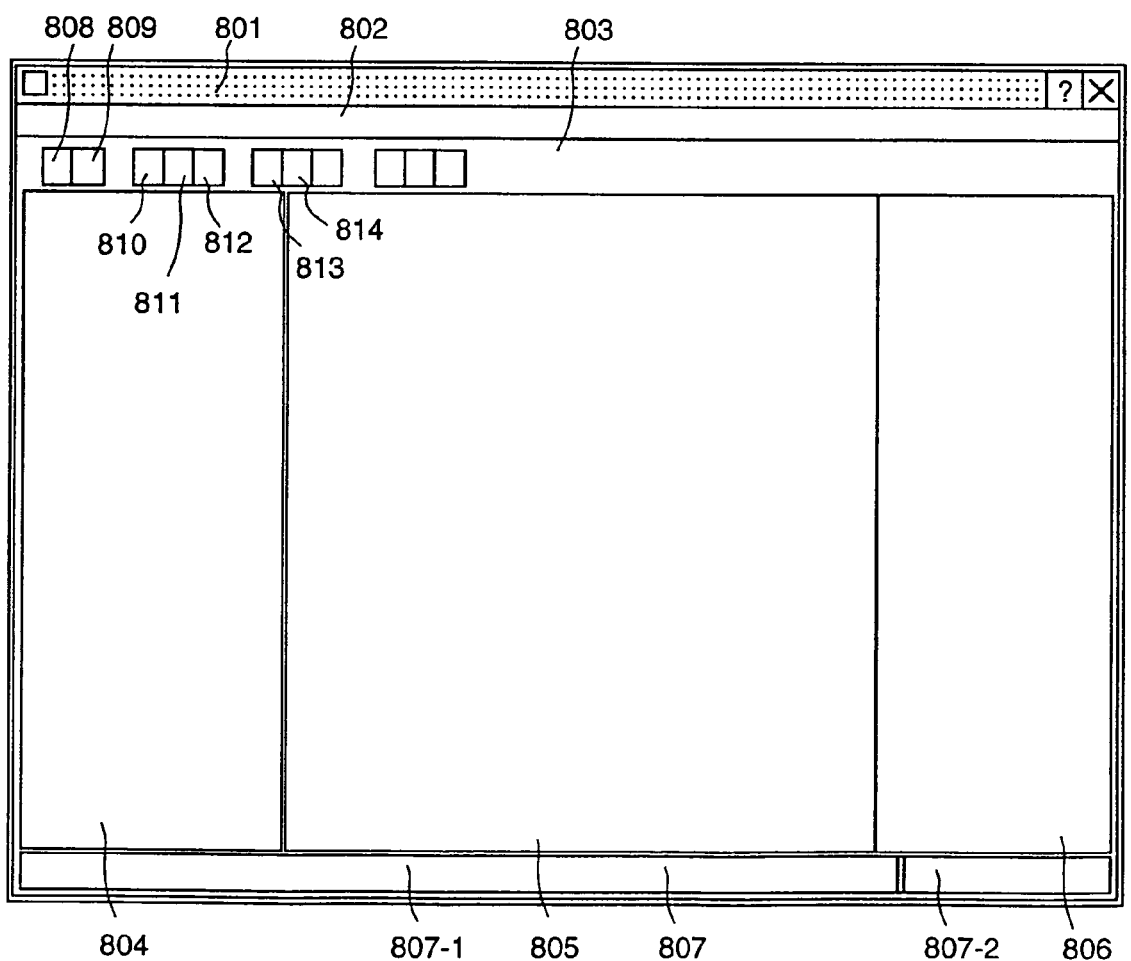
FIG. 8 is a diagram indicating a basic layout of a displayed on the display section in the biomagnetic instrument of FIG. 1.

FIG. 8 shows a basic lay-out of the screen displayed on display unit 8-1 of FIG. 1. The upper portion of the screen is occupied, from the above sequentially, by a title bar region 801, a menu bar region 802 and a tool bar region 803 with icons. Each region described above may be considered to be a display region or area. This basic lay-out of screen arrangements is displayed commonly on respective screens for other objects of processing, for example, in the registration of patients, patient data reading, biomagnetic field measurement, data analysis or the like. Therefore, ease-of-use is facilitated, and measurement and processing times are substantially reduced.

The center area of the screen is occupied, from left to right, by patient information section 804, analysis data section 805 for displaying analysis data such as graphs and waveforms, and operating region section 806. Further, the bottom portion of the screen is occupied by status bar 807, which includes a message bar section 807-1 which is on the left side thereof and displays a guide message descriptive of the next operation, and a date/time indicator 807-2 which is located on the right side thereof. By way of example, these message bar section 807-1 and date/time indicator 807-2 may be included in one display region.

In the screen of this embodiment of the invention there are constantly displayed in the upper portion, title bar section 801 descriptive of the title of its system, menu bar section 802 for executing basic operations of this system, and tool bar section 803 which displays related operations in this menu bar section 802 the occurrence of which is frequent for facilitating ease-of-use. Therefore, the operator is not required to search for the operation area every time the screen is changed, and can learn a current system in operation easily by looking at the uppermost portion of the screen. In addition, because the uppermost portion of the screen is an eye-catching portion the operator looks at initially as is the case of reading a book or paper, provision of the basic items required for operating the system in the uppermost portion will improve the ease of use in the most human-friendly and natural way. Further, because the analysis data display section 805 which is a main part of the screen is disposed in the center portion of the screen occupying a large area thereof, its visibility is improved. Because the operating area section 806 specific to a current screen is disposed to the right of the main part of the screen, the identical positional relationship between the main display area and the operating area which is suitable for the right-handed operator is provided thereby facilitating smooth and natural operation. Therefore, if this screen arrangement is adopted in a screen provided with a touch panel, the right-hand of the operator at work on its operation area section 806 will not disturb monitoring of its analysis data display section 805. Still further, because the patient information section 804 the main function of which is for patient confirmation is disposed to the left side of the analysis data display section 805, the operator is ensured to be able to carry out every operations always confirming the patient. In addition, because this left side position is remotest from the right-hand side operation section, it will not disturb the visibility of the screen even if this is adopted in the screen provided with the touch panel.

Further, only when a patient list and its patient's data list are to be displayed, these analysis data display section 805 and operation area section 806 are replaced by them (see FIG. 24). When a patient list screen (FIG. 24) is displayed, patient information corresponding to a patient marked with a cursor in the patient list on display is displayed always in the patient information section 804. Further, when analysis data such as graphs and waveforms are displayed in the analysis data display section (FIGS. 25–34), patient information corresponding to the patient for whom the analysis data on display are obtained is always displayed in the patient information section 804. From these information, a relationship between the displayed analysis data and a particular patient for whom the analysis data are obtained can be identified. As described above, because the patient information section 804 is always displayed at a predetermined position (left side) on the screen of the system in the same way as the menu bar section 802, the operator does not need to search for the patient information area every time the screen changes, and can identify readily by looking at the predetermined position (left side) in the screen.

In the title bar, its frame title, more specifically, "Multichannel MCG System" is displayed (FIGS. 24–34). Operation elements such as buttons and text frames are disposed in the operation area section 806. The menu bar section is where a desired operation menu is selected, and which menu includes "File(F)", "Edit(E)", "List(L)", "Measurement(Q)" (or "Data Acquisition(Q)"), "Data Analysis(A)" and "Help (H)", and which are arranged in sequences of operation.

Figure 9:
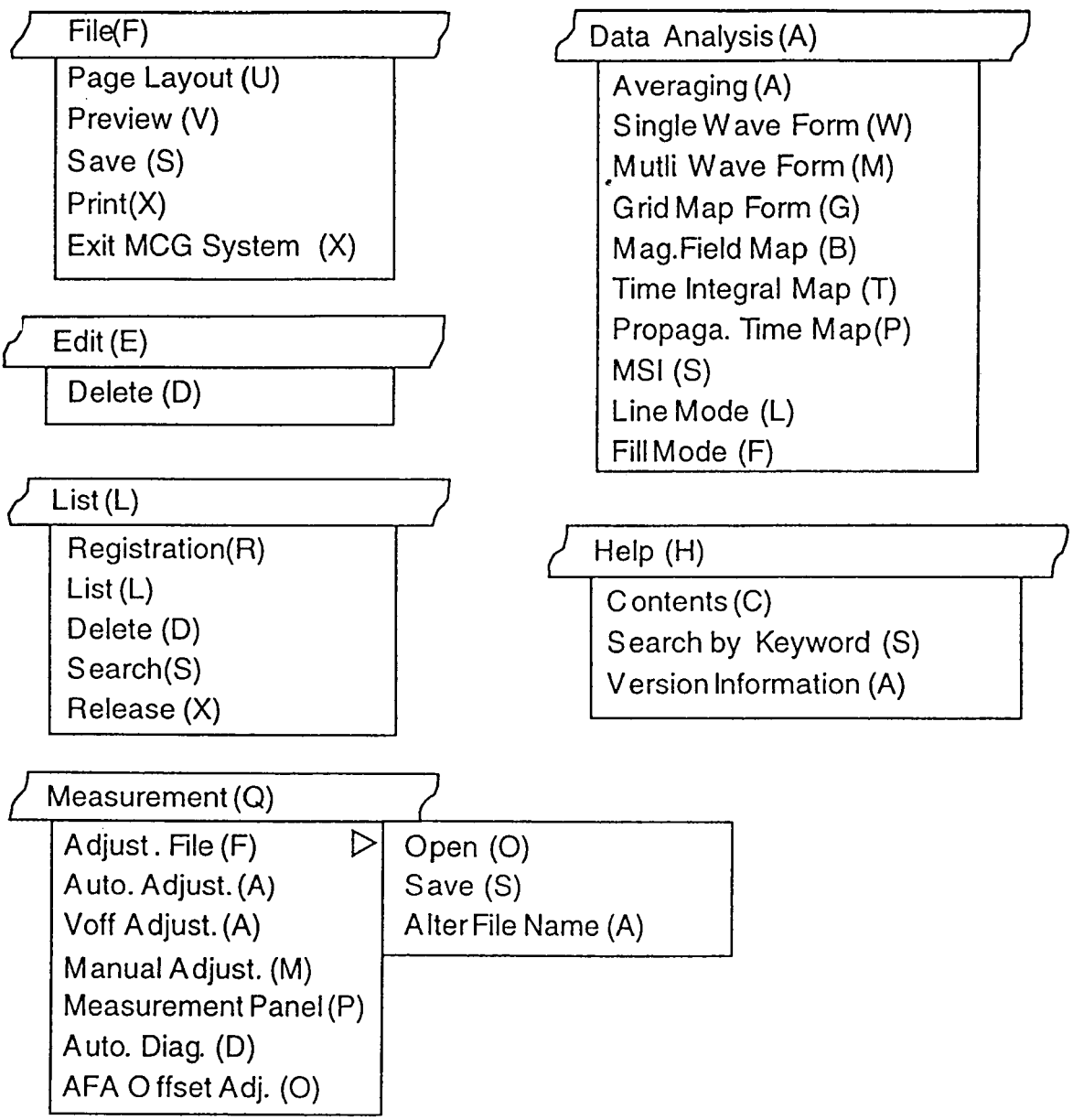
FIG. 9 is a diagram showing operation menu in the menu bar in the displayed in the display section in the biomagnetic instrument of FIG. 1.

FIG. 9 shows contents of respective operation menus in the menu section on the screen, and these menu are displayed as pull-down menus by clicking their corresponding menu buttons, respectively. Therefore, when these pull-down operation menus are not required, only their keywords descriptive of their respective menus are displayed in the menu bar section, thereby allowing for the analysis data section and the operation area section to have a wider display area. When a certain operation menu is required for a certain operation, one of the above-mentioned keywords which are arranged in the sequence of operation is selected accordingly from the menu bar section to be displayed for designation of its operation. Because these keywords are arranged therein from the left to the right in the order of spelling of characters, natural and smooth designation of its operation can be assured.

The pull-down menu from "File(F)" includes: "Page Layout (U)" item which sets up a page layout by opening a page layout dialog frame (not shown); "Preview (V)" item for previewing prior to printing; "Print (P)" item for data printing; and "Exit(X)" to exit from the multichannel MCG system.

The pull-down menu from "Edit(E)" includes "Delete (D)" item. Measurement data of the patient in the patient list on the patient list screen (FIG. 24) is displayed on the data list thereof, and the item "Delete(D)" is for deleting a portion of data in the data list marked by the cursor. Thereby, the data to be deleted must be selected in advance. When this menu is clicked, a confirmation dialog frame is opened requesting confirmation whether "Delete" is to be executed or not. When "Delete" is required, a button "OK" in the dialog frame is clicked, and when "Delete" is to be canceled, a button "Cancel" is clicked. By provision of this confirmation dialog frame operation, inadvertent operation by the operator to delete the data will be prevented.

The pull-down menu from "List(L)" includes as its items "Registration(R)", "List(L)", "Delete(D)", "Search(S)", and "Release(X)". When "Registration(R)" button is clicked in the pull-down menu, a patient registration dialog frame shown in FIG. 10 is opened. This dialog frame is used for entering data items relating to the patient. These data items that can be entered include registration date, ID number of the patient up to a predetermined count of digits, name, date of birth, height, weight, sex, disease classification information, and comments on the patient. When "Registration" button is clicked in that dialog frame, all data having been entered are registered, and simultaneously the input frame is cleared ready for re-entry operation, and when "Cancel" button is clicked, all the input frames are cleared, then when "Exit" button is clicked, the patient registration dialog frame is closed.

When "List(L)" is clicked in the pull-down menu, the patient list (FIG. 24) is displayed. When "Delete(D)" in the pull-down menu, which is for deleting the patient in the patient list (FIG. 24) marked with the cursor, is clicked, a confirmation dialog frame is opened prior to its deletion requesting confirmation whether its delete operation is to be executed or not, and when its deletion is required, "OK" button in that dialog frame is clicked, and when its deletion is to be canceled, "Cancel" button therein is clicked. When any designated patient is deleted, every data in the data list of the designated patient are deleted simultaneously.

When "Search(S)" is clicked in the pull-down menu, a search dialog frame indicated in FIG. 11 is displayed. After searching a designated patient and its data, only the designated patient and its data having been searched are displayed on the patient list. A search target regarding the patient and data includes all the patients and their data. Patient name, date of registration, sex, class of data, measurement date, diagnosis, comment, inspector, body position, and the like are used as a keyword for the search of the data. A multiple facet search is possible based on a combination of a plurality of keywords described above. "Release(X)" in the pull-down menu is used for releasing an exclusive display of the searched patient and its related data from the and for displaying the whole patients and the whole data thereon.

The pull-down menu of "Measurement(Q)" includes items of "Adjustment File(F)", "Automatic Adjustment(A)", Voff Adjustment(V)", "Manual Adjustment(M)", "Adjustment File(F)", "Measurement Panel(P)", "Sensor Diagnosis (D)", and "AFA Offset Adjustment(O)".

When "Adjustment File (F)" is clicked, a sub pull-down menu thereof is opened, which includes "Open (O)", "Save (S)", and "Alter File Name (A)" items. "Open (O)" in the sub pull-down menu is used to open a system adjustment (FIG. 34), and set up system adjustment values, i.e., Ibias and Voff for the system through a designated adjustment file which is opened. "Save (S)" is used to open the confirmation dialog frame and to save the adjustment value in the adjustment file by overwriting the updated data over the obsolete data. "Alter File Name (A)" is used for saving the current adjustment data in another adjustment file by altering its name.

When "Automatic Adjustment (A)" is selected in the pull-down menu, the system adjustment screen (FIG. 34) is displayed, then bias current Ibias and off-set voltage Voff in FLL circuit 6 are automatically adjusted in accordance with the flow of FIG. 22 to be described later. When "Voff Adjustment (V)" is selected, the system adjustment screen (FIG. 34) is displayed, and the off-set voltage Voff of FLL circuit 6 is automatically adjusted according to the flow of FIG. 23 which will be described later. When "Manual Adjustment (M)" is selected, the manual adjustment dialog frame of FIG. 12 is opened. Using the scroll bar and mouse, the operator can select any channel, and modify its bias current Ibias and off-set voltage Voff. If entered values are correct and appropriate, "OK" button is clicked to set up the values. When "Cancel" button is clicked, the modification becomes invalid, then this dialog frame is closed.

When "Measurement Panel (P)" is clicked, a measurement screen which includes a grid map (FIG. 25) is displayed. When "Sensor Diagnosis (D)" is clicked, an automatic diagnosis dialog frame as shown in FIG. 13 is opened. In the sensor diagnosis or automatic waveform diagnosis step, parameters of the Φ-V characteristic curve in the of FIG. 34 to be diagnosed such as its amplitude, center value and cycle thereof are automatically checked for their validity, and any channel which is outside a designated range of the measurement is notified to the operator as an event of an inappropriate state unfit for the display of the Φ-V characteristic curve or for updating the status of the same curve. When any channel the state of which is not suitable for measurement is detected, an error dialog frame is opened to display an error message and notify it to the operator. This unsuitable state of the channel may be notified also by displaying the Φ-V characteristic curve of that channel in a different color. Here, in the case a minimum value of the Φ-V characteristic curve is automatically checked, the unsuitable state unfit for measurement refers to a state where a difference (subtraction) between the maximum value and the minimum value in the Φ-V characteristic curve is smaller than the minimum amplitude detected. In the case the center value is specified, the unsuitable state refers to a state where an absolute value of averages of the above-mentioned maximum values and the minimum values is larger than the specified center value. In the case its cycle is specified, the unsuitable state of measurement refers to a state where the cycle of Φ in the Φ-V characteristic curve is outside the range defined by the first text frame (a lower limit) and the second text frame (an upper limit). In order to validate automatic diagnoses of the minimum value of amplitude, the center value and the cycle, respective check frames on the left side of respective items may be checked using the mouse to indicate "x" mark therein, then a desired value may be entered through the text frame corresponding thereto. Automatic diagnosis parameters entered as above become effective upon clicking "OK" button, and this dialog frame is closed. When "Cancel" button is clicked, the entered parameters become invalid, and the dialog frame is closed. "AFA Offset Adjustment (O)" is used when adjusting off-set voltage Aoff of AFA 7, and when "AFA Offset Adjustment (O)" is clicked, a measurement (FIG. 25) which belongs to the single wave display is displayed.

The pull-down menu of "measurement (AQ)" includes "Averaging (A)", "Single Channel Wave Display (W)", "Multichannel Wave Display (M)", "Grid map Display (G)", "Mapping of Magnetic Flux (B)", "Time integral mapping (T)", "Mapping of Distribution of Propagation (P)", "Magnetic Source Imaging (S)", "Line Mode (L)", and "Fill-in Mode (F)".

When "Averaging(A)" is clicked, an averaging screen (FIG. 27) is shown, when "Single Wave Display (W)" is clicked, a single waveform screen (FIG. 28) is shown, when "Multichannel Waveform display (M)" is clicked, a multichannel waveform screen (FIG. 29) is shown, and when "Grid map display (G)" is clicked, a grid map screen (FIG. 30) is shown, respectively, then a check mark (x) indicative of its selection is shown on the left side of its menu. Further, when "Mapping of magnetic flux (B)" is clicked, a map of magnetic field screen (FIG. 31) is shown, when "Mapping of Time Integral (T)" is clicked, a map of time integral screen (FIG. 32) is shown, and when "Mapping of distribution of propagation (P)" is clicked, a map of distribution of propagation (FIG. 33) is shown, respectively, and a check mark (x) indicative of its selection is shown on the left side of its menu. Still further, when "Magnetic source imaging (S)" is clicked, an inverted triangle mark is indicated on the left side of its menu, and a magnetic source approximated by a current dipole is superimposed on the map of magnetic flux (not shown). As for the mapping of magnetic flux, time integral mapping, mapping of distribution of propagation, and magnetic source imaging, when "Line mode (L)" is selected, respective lines on their screens are displayed with their gaps between lines not painted or filled in, and when "Fill-in mode (F)" is selected, their screens are displayed with the gaps between respective lines filled in. In order to indicate a current-state mode selected, a check mark indicative of its selection is shown on the left side of its menu.

The pull-down menu of "Help (H)" includes "Contents (C)", "Search by Keywords (S)", and "Version Information (A)", which are used for indicating the contents, searching a topic by way of a keyword, and opening a version dialog screen, respectively.

In the tool bar 803, there are disposed icons for "Patient Registration" (808), "Patient List" (809), "Print" (810), "Preview" (811), "System Adjustment" (812), "Measurement" (813), and "Data Analysis" (814). These icons are linked with menu functions, and these icons designated can be chosen from their pull-down menu items according to their frequencies of use although the illustration of which is omitted. Namely, "Patient Registration" (808) corresponds to "Registration (R)" of "List (L)"; "Patient List" (809) corresponds to "List(L)" of "List (L)"; "Print" (810) to "Print (P)" of "File (F)"; "Preview" (811) to "Preview (V)" of "File (F)"; "System Adjustment" ((12) to "Manual adjustment (M)" of "Measure (Q)"; "Measure" (813) to "Measurement Panel (P)" of "Measurement(Q)"; and "Data Analysis" (814) to "Grid map display (G)" of "Data analysis (A)", respectively. As for the menu which is linked with its icon, this menu can be opened directly by clicking its icon.

Any operation the frequency of its use is high, and which is provided with an icon displayed abutting to the analysis data, can be accessed easily by clicking its icon, therefore, its operation through its icon which is more easy to recognize and handle than through the operation of the above-mentioned menu bar can facilitate its operation. Further, the above-mentioned icons can be selected for display at discretion by the operator, or may be automatically displayed on the tool bar section 803 in accordance with the frequency of its use.

Now, with reference to FIGS. 14–34, a series of operations including the system adjustment, the registration of patients, measurement on the patients registered, to the data analysis of thus obtained data, will be described in the following.

Figure 16:
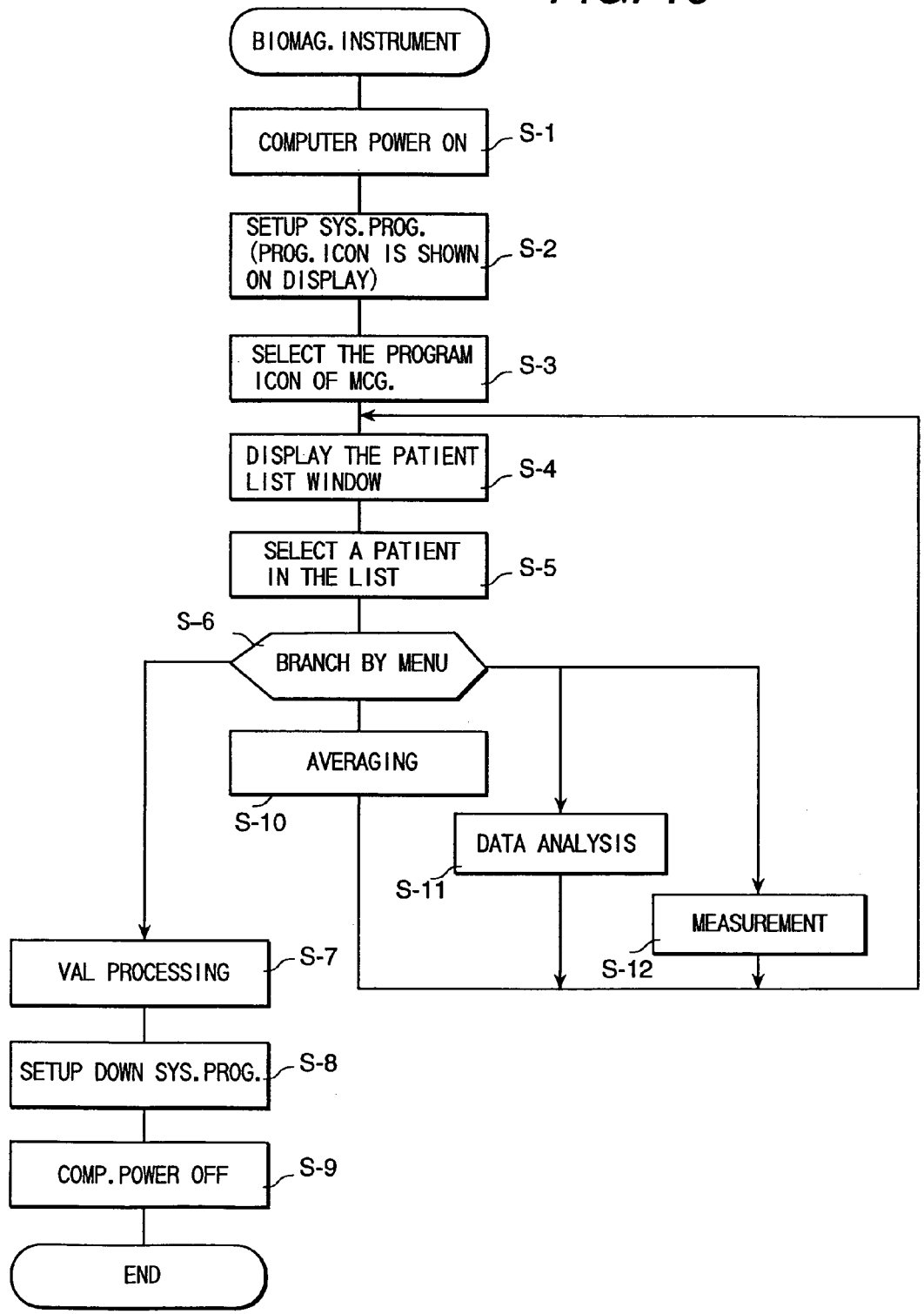
FIG. 16 is a schematic flowchart indicating the steps of operation executed in the biomagnetic instrument of FIG. 1.

FIG. 16 shows a schematic flowchart of operations according to the invention. When the power of computer 8 is turned on (step S-1), the operating system is set up, and a program start icon is displayed on 8-1 (S-2). When a multichannel MCG system program icon is selected in step S-3, the patient list screen indicated in FIG. 24 is displayed (S-4).

In the system according to this embodiment of the invention, as an initial at the time of system set-up, the patient list screen of FIG. 24 is displayed. This is because that the data management in this system is executed via the patient information as its keyword since a relationship linking between a particular patient and his/her detected data or analysis data is considered very important. That is, because management of the detected data and analysis data cannot be executed without the patient information. Thereby, in this system, a patient is registered at first through the patient list screen, or when the patient is already registered, the patient is designated on that screen, then the step advances to the measurement step in the case of data updating, alternatively when there exist data having been detected, a target data is specified thereon. By way of example, a set-up wait time screen indicating a wait time required for the system set-up may be displayed prior to display of the patient list screen, or a screen to display the contents of the system may be provided as well.

In the patient list screen of FIG. 24, the left side thereof is occupied by the patient information area, and in the upper portion of the right side area thereof is displayed a patient list, and in the bottom portion of the right side area thereof is displayed a data list. Respective items displayed in the patient information area on the left side are the same as described with reference to FIG. 10. Items in the patient list in the upper portion include ID (patient's ID number), name, date of registration (date of data entry), measurement counts (the number of measurement executed), date of birth, age, height, weight, comments (regarding the patient) and so on. The patient list can be scrolled up and down with a vertical scroll bar, and the items of the patient list can be scrolled horizontally with a horizontal scroll bar. A selected row of a patient is displayed in an emphasized mode.

Items in the data list on the patient designated include ID, type of data (raw data or averaged), sampling interval (sampling interval of signals in ms during measurement), sampling time (s), classification (disease classification information), date and time of measurement, comments on data, and the like. The data list can be scrolled up and down with a vertical scroll bar, and the items of the data list can be scrolled horizontally by a horizontal scroll bar. A row of data selected is displayed in emphasized mode.

According to this patient list, a row of information for each patient is displayed in the patient list. Thereby, information of each patient can be clearly distinguished from that of other patients arranged vertically thereby improving discrimination therebetween, and thereby preventing inadvertent operation such as to select a wrong patient. This information on each patient can be scrolled horizontally by the horizontal scroll bar, and information on the designated patient can be displayed item by item vertically in the patient information area without limiting its visibility. The visibility may be further improved by arranging such that the items in the data list on each patient can be scrolled vertically or horizontally. Further, by displaying information for each patient in a row, a many number of patients can be monitored at once, thereby reducing the frequency of scrolling using the vertical scroll bar. Still further, by a simple operation to click the cursor which is moved to a target patient on the patient list, the data on the target patient can be displayed readily in the data list area in the bottom portion. Moreover, because the patient list and the data list areas are disposed in vertical directions such as to minimize eye movements, their relevance can be recognized easily. Still further, because size of the data list area can be changed easily through a simple operation of the cursor, i.e., by moving the cursor to the upper edge of the data list area and dragging upward the same, the size of its area can be increased in accordance with the number of list items in the data list.

In step S-5, a desired patient's row is selected from the patient list on the patient list screen. In the case of averaging process which will be described later, a raw data line is selected always. In the next step S-6, the flow can be branched to four sub-menus by menu selection. One of which is to select a submenu "End of magnetocardiograph (X)" from the menu "File (F)". Upon selection of this sub-menu, final processing to close the screen is executed (S-7), and thereby shutting down the system (S-8). Then, the power of computer 18 is turned off (S-9) to compete the flow.

According to the other sub-menus, averaging process (S-10), data analysis (S-11), and measurement (S-12) are executed. The averaging process is enabled through selection of a sub-menu "Averaging (A)" in the menu "Data Analysis (A)". Further, the data analysis is enabled by selecting any one of the submenus of "Single Wave Display (W)", "Multichannel Wave Display (M)", "Grid Map Display (G)", "Contour Mapping of Magnetic Flux (B)", "Contour Map of Time Integral (T)", "Propagation Time Contour Mapping (P)" and "Magnetic Source Imaging (S)" in the menu of "Data Analysis (A)". Further, the measurement is enabled by selecting the submenu "Measurement Panel (P)" in the menu "Measurement (Q)". After completion of steps S-10, S-11 and S-12, the flow returns to step S-4. Regarding the selection of a patient in step S-5, the averaging process in step S-10, the data analysis in step S-11, and the measurement in step S-12, their detailed descriptions will be made with reference to FIGS. 17–20 in the following.

Figure 17:
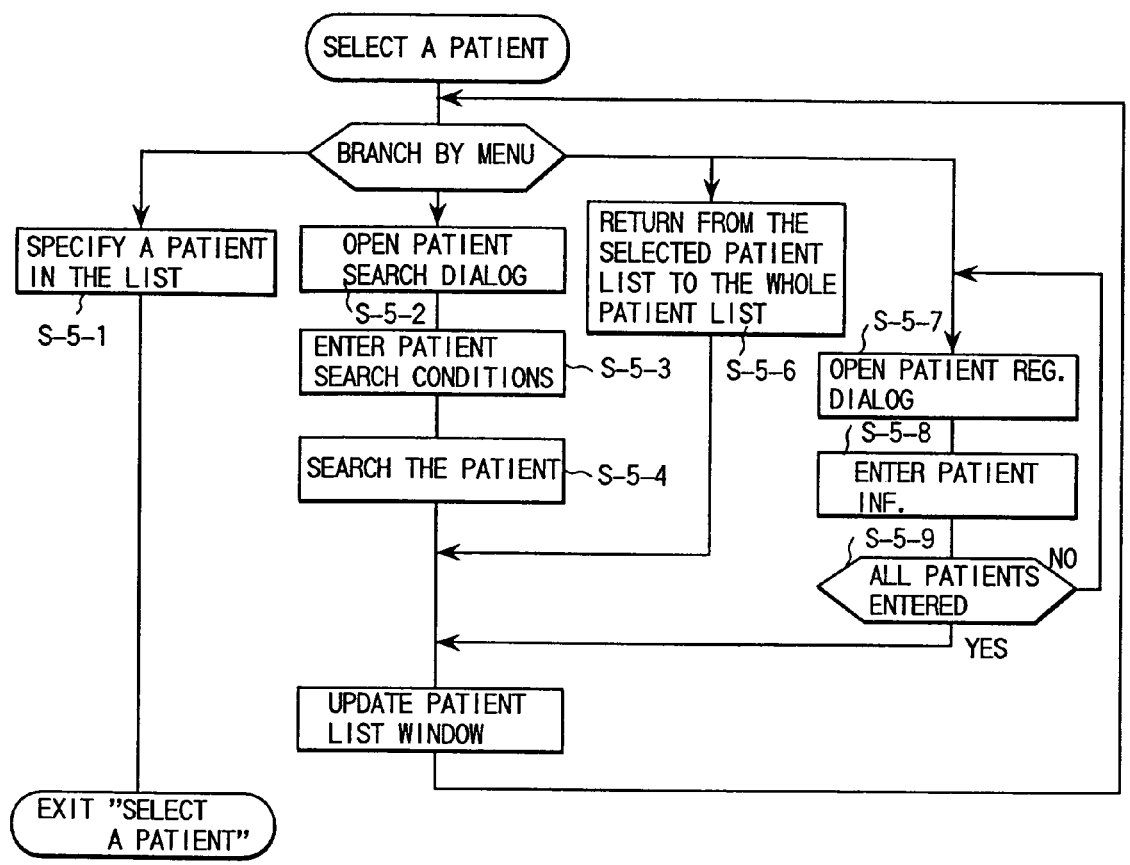
FIG. 17 shows a patient selection flow of the patient selection step in the operation flow of FIG. 16.

FIG. 17 shows the flow of the patient selection in step S-5 in FIG. 16. In this case of the patient selection, its flow is branched into four sub-menus by menu selection or by patient selection. One of them is to select step S-5-1 and specify a patient whereby completing the patient selection flow. According to another branch sub-menu, the sub-menu "Search (S)" in the menu "List (L)" is selected. Thereby, the search dialog frame shown in FIG. 11 is opened (S-5-2), and through this dialog frame, patient search conditions are entered (S-5-3). Thereby, the target patient is searched (S-5-4), and accordingly the contents of the patient list displayed on the patient list screen shown in FIG. 24 are updated (S-5-5). According to still another branch submenu, the sub-menu "Release (X)" is selected in the menu "List (L)". In this case, the selected patient is released to return to the whole patient list (S-5-6), the contents of display for the patient list are changed (S-5-5). According to the remaining branch sub-menu, the sub-menu "Registration (R)" is selected in the menu "List (L)". In this case, the patient registration dialog frame shown in FIG. 10 is opened (S-5-7), and through which patient information is entered (S-5-8). As to these steps, judgment of completion of data entry is executed for every patients until all data are entered (S-5-9), and upon completion thereof, updating of the patient list is executed (S-5-5).

According to this embodiment of the invention, except for the name and address of the patient or the like which are to be entered in characters, a plurality of input data or operation instructions to be entered are displayed selectively on the screen or may be displayed thereon by means of the pull-down menus, thereby allowing input operation of a selected object to be readily entered by designating the same using the mouse. Thereby, because almost every manual data entry operations required for this system can be executed using the mouse, it can offer a user-friendly environment, easy-to-operate even by such an operator who is not accustomed to keyboard operation, and reduce the time required for data entry and operation as well. Further, because the plurality of objects or targets for selection in the pull-down menus are preset in advance in the system or provided in the state allowable for their entry or operably, and are readily displayed, inadvertent input or operation can be prevented. Still further, in this embodiment of the invention, because it is allowed for the operator to enter additional data on the input area at a place designated by the cursor and through the keyboard operation, flexibility of data input is ensured for the operator. Although character input by means of the keyboard operation is contemplated in this embodiment of the invention, it is not limited thereto, and a dialog of the keyboard for data input may be displayed on the screen to be operated by the mouse, further a hand-written input dialog may be displayed to be operated by the mouse, or the may be provided with a touch-panel input device through which data can be input manually by hand or an input pen. By provision of such arrangements, the ease-of-operation in data input can be improved substantially.

Figure 18:
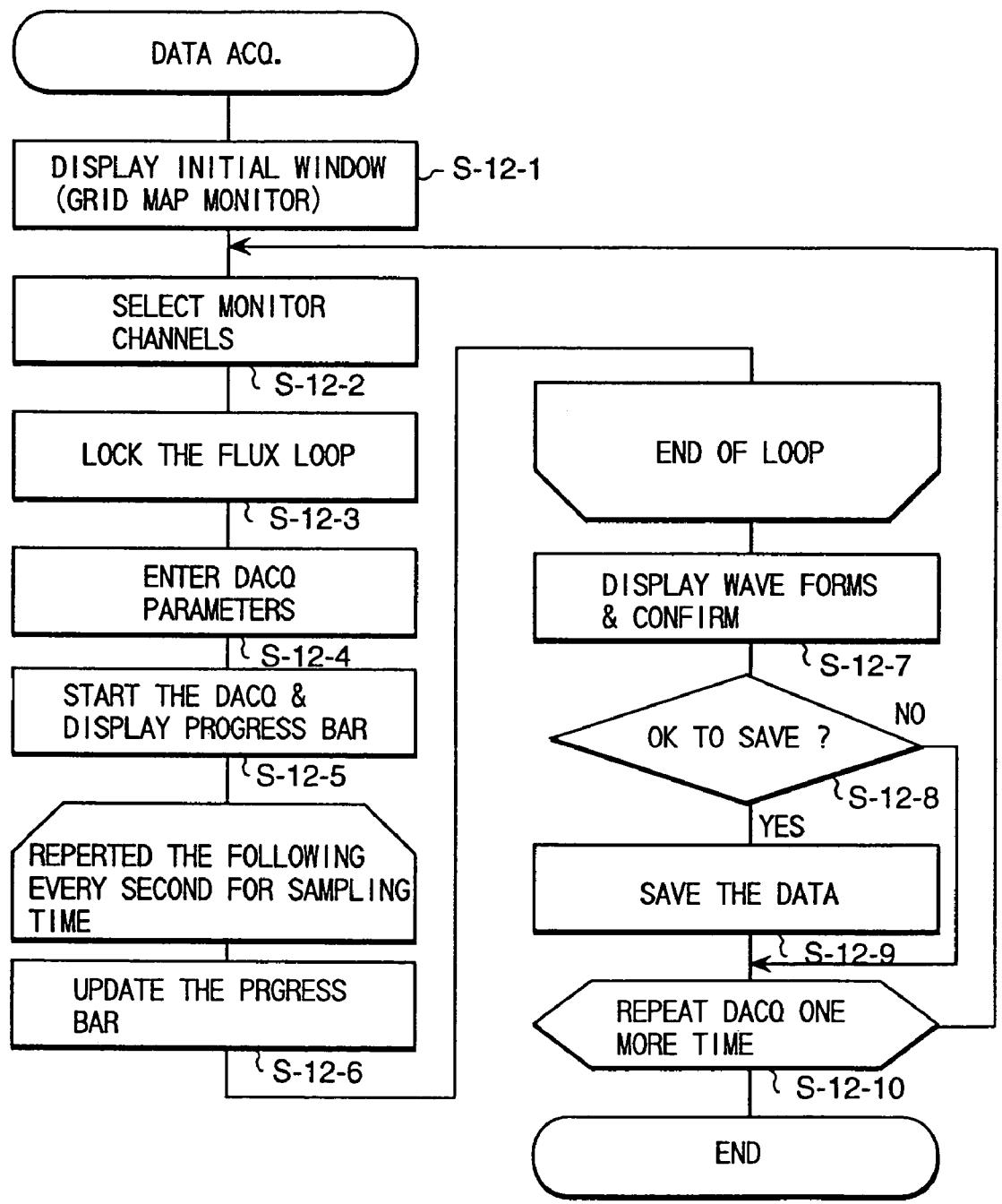
FIG. 18 is a flowchart indicating the flow of measurement in the measurement step in FIG. 16.
Figure 25:
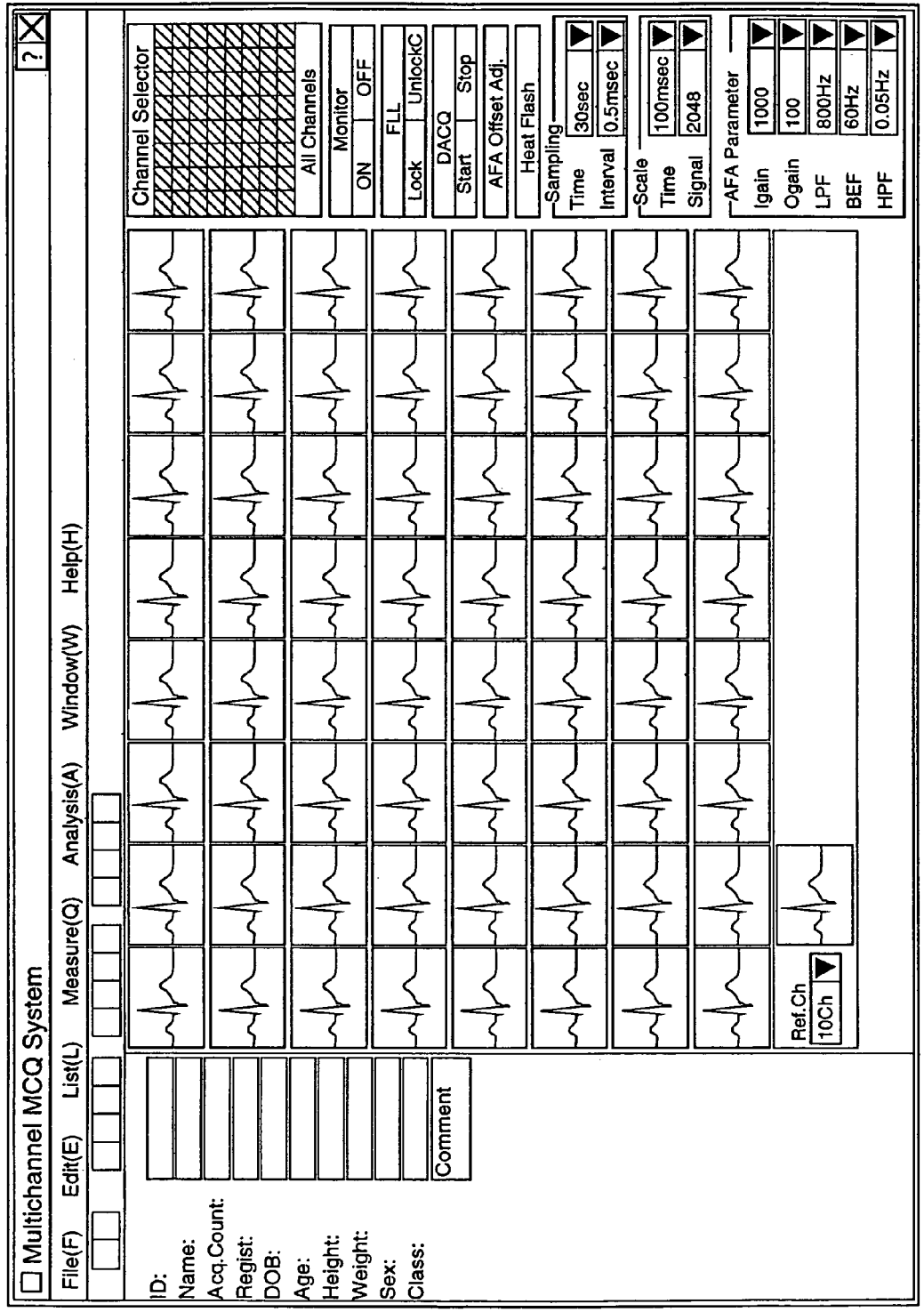
FIG. 25 shows a measurement screen displayed on the display section of the biomagnetic instrument of FIG. 1.

FIG. 18 shows a flow of measurement in step S-12 in FIG. 16. At first, a grid map of cardiomagnetic waves of FIG. 25 is shown as its initial (S-12-1). In the operation area section of FIG. 25, it is allowed to execute respective operations of channel selection, ON-OFF of the waveform monitor, lock/unlock of FLL circuit 6, automatic adjustment of offset voltage of AFA7, and heat flashing. It is also possible to set up signal sampling conditions, waveform display scale, and AFA parameters.

Figure 26:
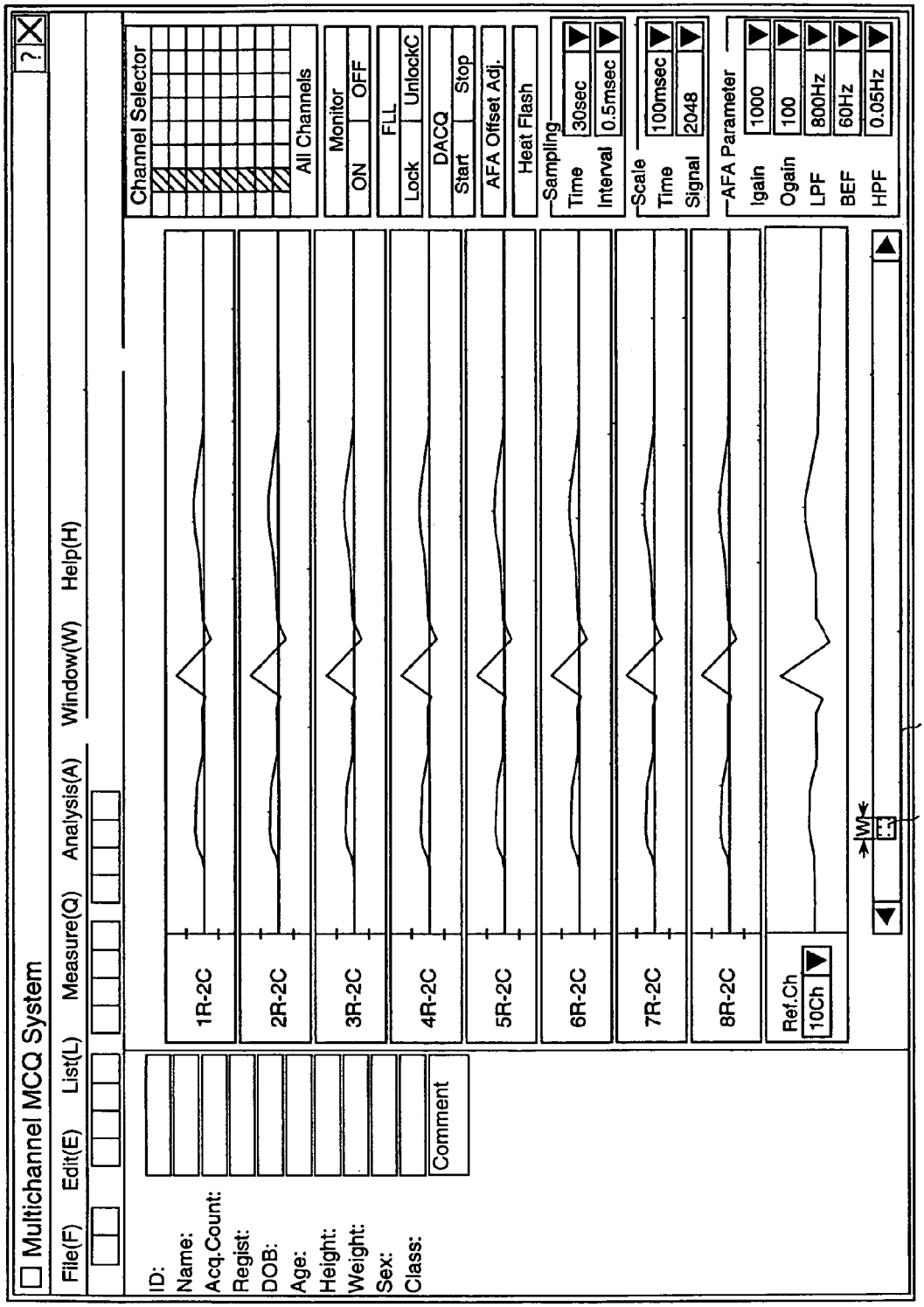
FIG. 26 shows a waveform confirmation dialog screen displayed on the display section of the biomagnetic instrument of FIG. 1 upon completion of measurement.

Its channel matrix includes 8×8=64 channels. All these channels can be selected by clicking "All Channel Select" button, or by dragging the cursor diagonally across the channel matrix. Further, these channels can be selected by a unit of a row or column by dragging any unit of row or column in the channel matrix. As for the selection of the channel matrix by a unit of row or column, this can be done by dragging any one of channels in a specified unit of row or column so as to select all the channels in that specified unit of row or column. In any case, a cardiomagnetic wave corresponding to any one of the channel items selected is displayed on the analysis data display area. In the case of channel selection by a row or column, they are displayed as shown in FIG. 26. In this case, designated waves are displayed in full scale at least on the time axis. Namely, in the case where all of the 64 channels are dragged, the analysis data display area is divided into a mesh so as to allow for all the channels to be displayed simultaneously as shown in FIG. 25, while in the case of channel selection per row or column, the analysis data display area is divided vertically into line sections each having a full scale time axis as shown in FIG. 26, thereby allowing their waveforms displayed in a familiar graph mode easy to recognize.

As for monitoring of these waveforms, when "ON" button is pressed, signals are read at a predetermined interval of time, for example, from 0.5 sec. to 2 sec., and updating of these waveforms is repeated in order to monitor the cardiomagnetic signals of the patient. When "OFF" button is pressed, updating of the waveforms is interrupted. Regarding the FLL, when "Lock" button or "Unlock" button is clicked, magnetic lock or its lock release can be executed for all 64 SQUID sensors. In this case, when either one of these buttons is pressed, its state is maintained until the other one of these buttons is pressed, thereby preventing inadvertent occurrence of a state which is not selected.

Figure 14:
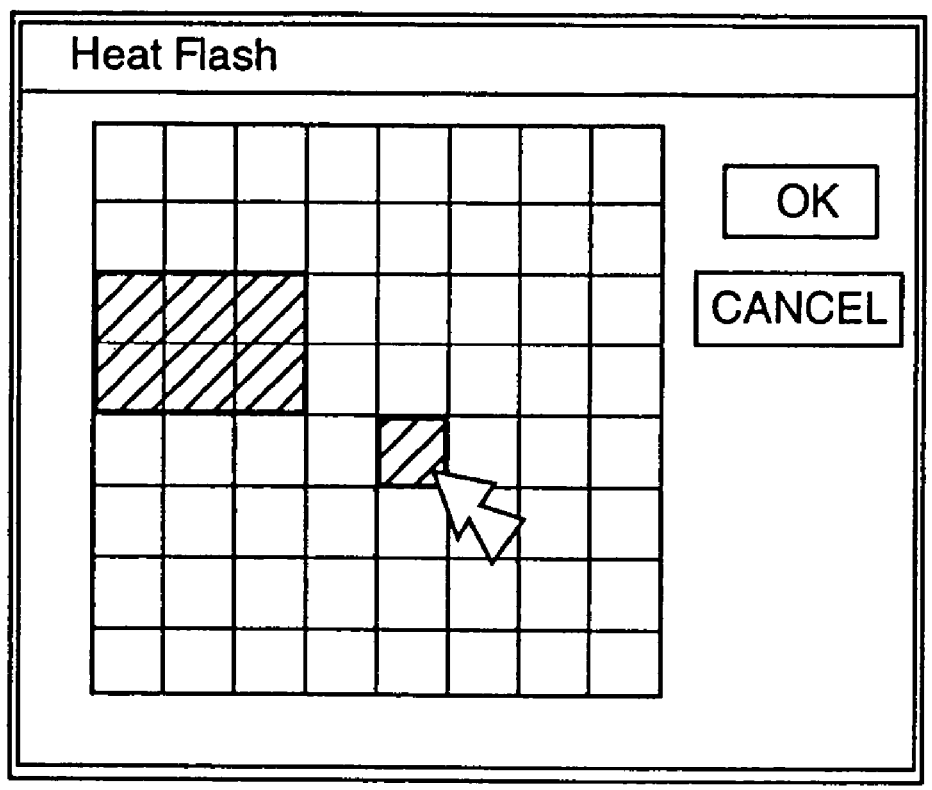
FIG. 14 shows the contents of a heat flash operation dialog frame which is opened when "heat flash" button is clicked on the screen of FIG. 25 or 26 to be displayed on the display section of the biomagnetic instrument of FIG. 1.

Further, when "AFA Offset Adjustment" button is clicked, its off-set voltage is automatically adjusted. Further, when "Heat Flash" button is clicked, the heat flash operation dialog frame indicated in FIG. 14 is opened. By selecting a channel with the mouse or an arrow key, and clicking "OK" button, a heat flash operation of the SQUID of the selected channel can be executed. By clicking "Cancel" button, the dialog frame is closed completing its process.

As for the time (measurement time) and its interval, a desirable value can be selected from selectively values in the pull-down menu which can be opened by clicking its corresponding text frame having an inverted triangle mark. These selective values for the time are, for example, 1 s, 5 s, 10 s, 30 s, 1 m, and 2 m, further as to the interval they are, for example, 0.1 ms, 0.5 ms, 1.0 ms, 2.0 ms, 4.0 ms, 5.0 ms and 10.0 ms. This time also may be set selectively between approximately 1 s and 24 hours when required. "Time" in "Scale" frame indicates a time scale in ms., i.e., horizontal scale, and "Signal" therein indicates an amplitude scale of signals after A/D conversion, i.e., vertical scale. These values also can be selected from selective values in a pull-down menu which is opened by clicking a corresponding text frame in the same way as in the case of the sampling time and interval setting.

The AFA parameter frame includes input gain Igain, output gain Ogain, cutoff frequency of low-pass filter (LPF), central frequency of band elimination filter (BEF), and cutoff frequency of high-pass filter. In the same manner, these values can be selected as desired from selective values or characters in their pull-down menus which can be opened by clicking corresponding text frames. As for input gain Igain, its value can be selected, for example, at 1, 2, 5, 10, 20, 50, 100, 200, 500 and 1000; as for output gain Ogain, it can be selected, for example, at 1, 10 and 100; as for the LPF, it can be selected, for example, at 30 Hz, 50 Hz, 80 Hz, 100 Hz, 200 Hz, 400 Hz and 1 kHz; as for the BEF, it can be selected, for example, at Off, 50 Hz and 60 Hz; and as for the HPF, it can be selected, for example, at 0.05 Hz, 0.1 Hz and through. By way of example, these values may be entered directly through the keyboard instead of the above-mentioned selection via their screens.

Further, in addition to the main 64 channels, auxiliary channels, for example, of 16 channels may be provided so that these auxiliary channels display, for example, electro-cardiograms. In the bottom portion of FIG. 25, there is displayed a waveform at the tenth channel as a reference channel. This waveform is an electrocardiogram obtained at the tenth channel of the auxiliary channels. Generally speaking, the cardiomagnetic wave includes a magnetic noise while the electrocardiogram does not includes such a noise. Therefore, through comparison of a cardiomagnetic wave with an electrocardiogram displayed in the reference channel, information regarding whether or not a magnetic noise is included in the cardiomagnetic wave can be obtained. Of course, this electrocardiogram may be obtained not from the auxiliary channels but from any of the normal 64 channels. Further, instead of this electrocardiogram wave, a brain wave, blood stream wave, blood pressure wave or the like may be used. Still further, it may be arranged such that an electrocardiogram wave of a pregnant woman is compared with a cardiomagnetic wave of a fetus. Further, the reference waveform is not limited to that of one channel, and a plurality of reference waveforms of a plurality of channels may be displayed. Still more, the reference channels displayed here are not limited to the signals from the patient, but various other signals from control devices may be displayed for the purpose of inspection and maintenance as well.

Again, with reference to the flow of FIG. 18, when the monitor channel is selected in step S-12-2 in the same manner as described, and FLL's lock button is clicked, magnetic flux lock of all the SQUIDs is executed in step S-12-3. In this condition, measurement parameters including sampling timing and signal setting, and AFA parameters are set up (S-12-4). This set-up process can be omitted in the subsequent event provided that the same parameter set-up conditions can be used, thereby minimizing the parameter set-up time in the subsequent event. Further, this parameter set-up conditions may be stored attached with titles easy to access.

Figure 15:
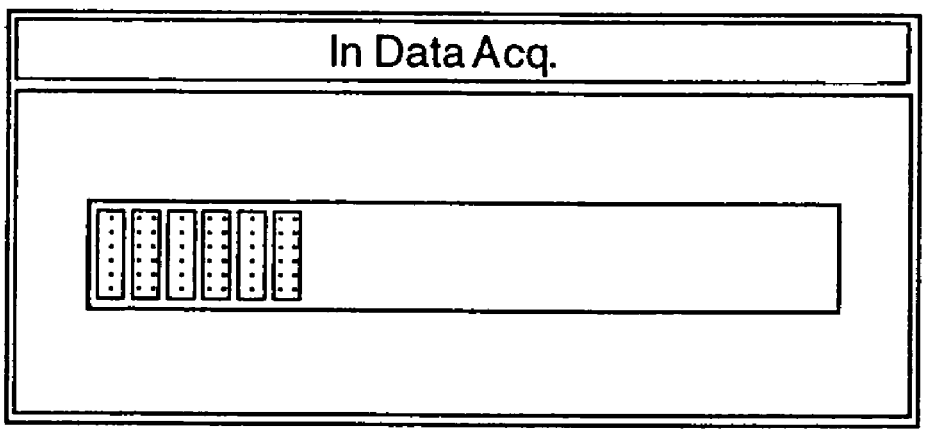
FIG. 15 shows a measurement progress bar which is displayed on the screen during measurement in the biomagnetic instrument of FIG. 1.

When "Start" button in "Measurement" frame is clicked, measurement operation is started, and "Measurement in Progress" screen of FIG. 15 is displayed together with a progress bar indicative of the state of progress of its operation (S-12-5). The progress bar in this embodiment of the invention is indicated as a bar graph which extends from the left to the right in the direction of its progress, however, it is not limited thereto, and it may be indicated as a circle or the like for indicating the degree of processing or time. Further, this progress bar is preferably displayed at a predetermined marginal position on the measurement screen such that its display does not disturb the display of the measurement screen so as to minimize any inadvertent operation.

When the measurement operation starts, signal waves on display are fixed as they are, and the progress bar is indicated on the fixed screen. Updating of the progress bar is repeated, for example, every second until its set time is up (S-12-6). When "Stop" button in "Measurement" frame is clicked, the measurement operation is stopped. When the measurement is complete, the screen of FIG. 26 is displayed for confirmation of their waveforms (S-12-7). Then, it is determined whether or not to save the data (S-12-8). When the data needs to be saved, menus of "File (F)"-"Save (S)" are selected, then its signal is saved, and added to the data list of the patient concerned (S-12-9). Then, it is determined whether or not the measurement operation is necessary once again including the case where the save operation is not required (S-12-10), if necessary, the above-mentioned steps are repeated, and if not, the whole steps of the measurement are completed. In this instance, menu selection so as to return to the screen of FIG. 24 is executed. By way of description, FIG. 26 indicates an example where channels of rows at the second column are selected.

In FIG. 26, a scroll bar 262 having a scroll frame which is movable is disposed in the bottom portion of the analysis data display area. Scroll frame 261 which is movable horizontally between the both ends of scroll bar 262 has a width w which represents a time scale. A time width between the both ends of the scroll bar 262 represents a measurement time. Therefore, a waveform displayed is an enlarged waveform of a part of the wave generated during a designated measurement time slit, said part of the waveform corresponding to the time scale w of scroll frame 261. Thereby, the operator is allowed to learn at a glance the time scale (the width of scroll frame 261) of a waveform currently displayed in part on the analysis screen in particular with respect to the measurement time (the width of scroll bar 262), and further whether its waveform belongs to the former half or the latter half portions of the measurement time slit, thereby capable of improving their visibility for recognition substantially. Still further, because the position of the scroll frame 261 and the waveform in display on the analysis data screen area are linked, it may be arranged such that the display region of the analysis data display area is moved by dragging the cursor positioned at the scroll frame 261 so as to allow for the waveform at the desired time to be displayed thereon. By such arrangements, the scroll bar 262 can be used for reviewing the contents and accessing to their detailed data as well as for confirmation of their waveforms at any specified time.

Figure 19:
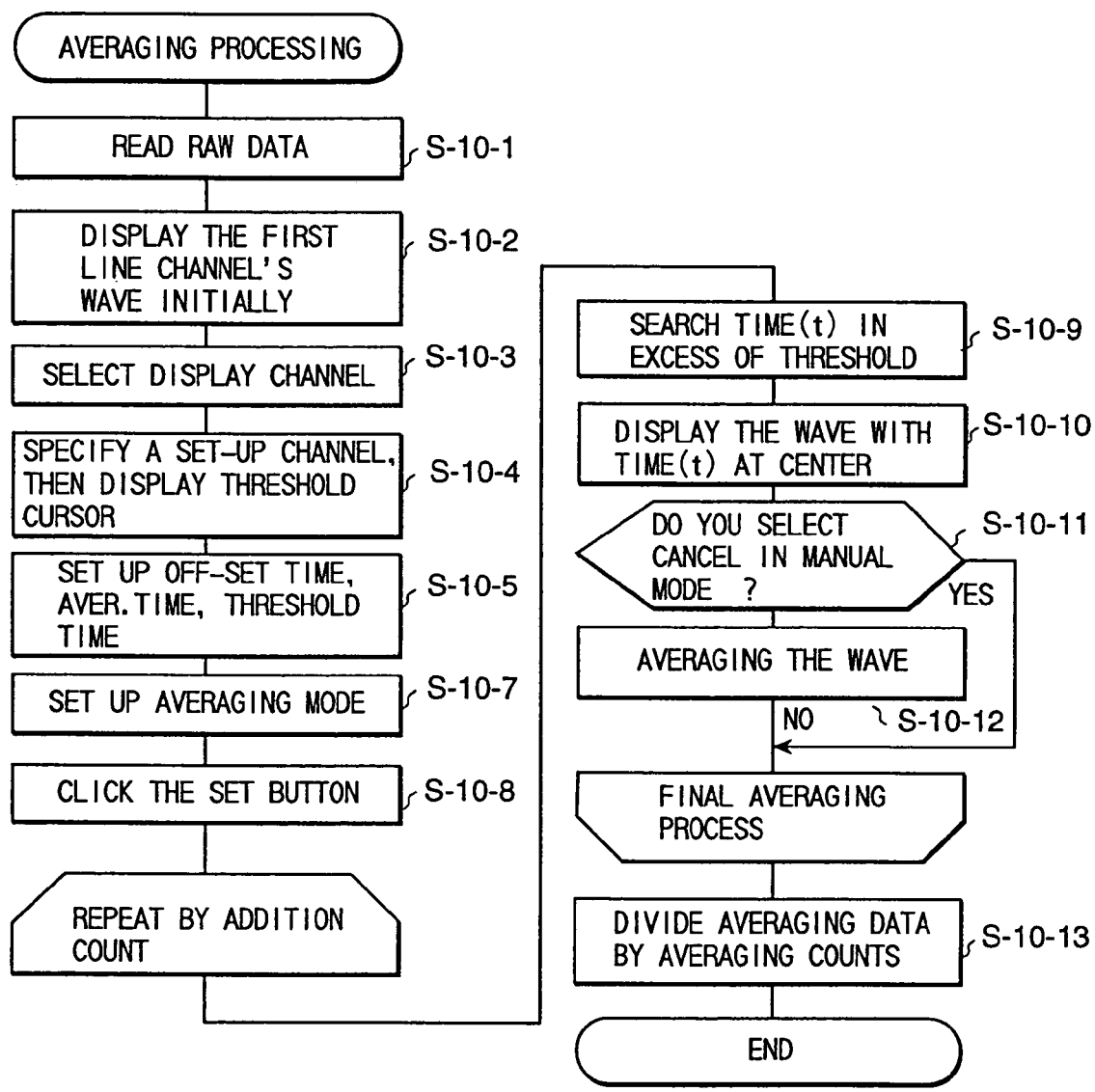
FIG. 19 is a flowchart indicating the flow of averaging in the averaging operation step in FIG. 16.

FIG. 19 shows a flowchart of the averaging process in step S-10 of FIG. 16. In the averaging process, in order to eliminate a noise in each data detected at each channel, data at each channel are added and an average thereof is computed. In order to set the base time for executing an averaging process for each channel, the following steps of processing are performed, then the averaging process of each channel is executed.

Figure 27:
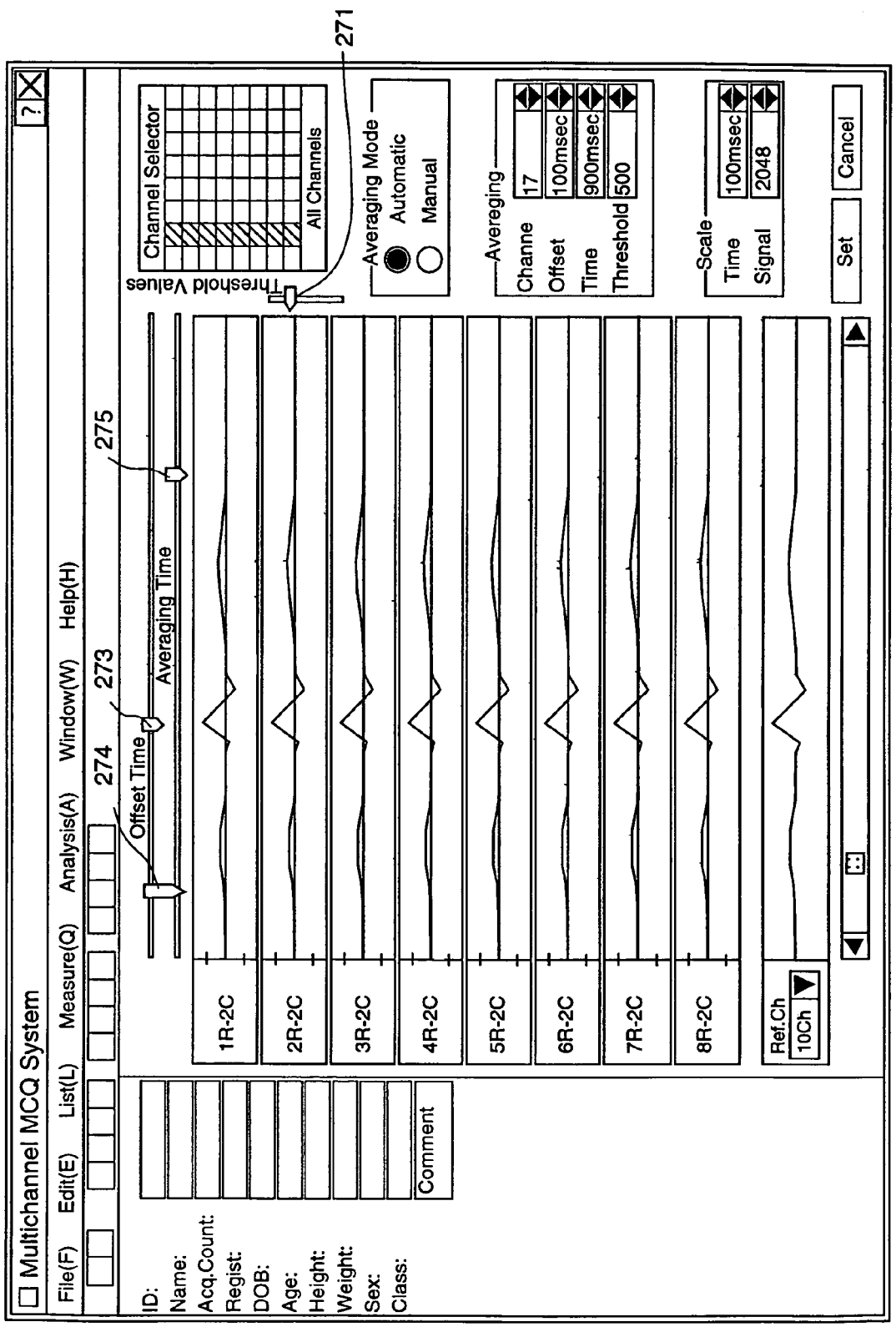
FIG. 27 shows an averaging screen displayed on the display section of the biomagnetic instrument of FIG. 1.

First of all, raw data of the designated patient is read in step S-10-1. This step is executed by clicking a line the "Data Type" of which is indicated as raw data in the list data in FIG. 24. Thereby, cardiomagnetic waves of respective channels in a first column are displayed as the initial display as shown in FIG. 27 (S-10-2). Then, a display channel is selected (S-10-3). By way of example, FIG. 27 shows a case where the second column channels are selected. Then, a set-up channel is specified (S-10-4). This step is executed by clicking "Channel" text frame in the "Averaging" frame provided in the operation region, or by clicking a particular area where the waveform of a desired channel is displayed using the mouse. In this case, when a triangle button in the text frame is clicked, the channel number increases, and when an inverted triangle button therein is clicked, the channel number decreases. FIG. 27 shows the case where its specified channel is at the second column and the second row. By this channel designation, a particular channel serving as the base time for its averaging process is designated. For this particular channel, a most typical channel or that having a waveform easy-to-see is preferably selected. If no appropriate channel having an appropriate waveform is available in the selected row or column, the flow can be returned to step S-10-3 to repeat the steps therefrom.

Further, when any one particular channel is designated on the analysis data display area, threshold cursor 271 is displayed indicative of the position of the designated channel as shown in FIG. 27. Thereby, the designated channel can be recognized visually for its confirmation. In FIG. 27, three slider cursors 273-275 are shown in the upper portion of the analysis data display area 805, which are automatically displayed at the same time when the of FIG. 27 is displayed.

In step S-10-5, a threshold value, off-set time and averaging time which are the averaging conditions are set up by clicking their corresponding text frames in the "Averaging" frame. Their digit number increases when the triangle button is clicked, and decreases when the inverted triangle button is clicked. Set-up of a threshold value is done by selecting an appropriate number indicative of its threshold in "Threshold" text frame. By this selection, threshold cursor 271 is automatically moved to the position corresponding to this digit number selected. This position of movement can be clearly confirmed on its cursor line. Because any change (selection) in the digit number indicative of its threshold in the "Threshold" text frame and the movement of the threshold cursor 271 are linked each other, its threshold can be set up also by moving the threshold cursor 271. Slider cursor 273 indicates a point of time (base time point) at which the rise portion of a wave coincides with the threshold which is set up by the threshold slider cursor 271, and this indicated position of coincidence can be clearly confirmed by its cursor line. The slider cursor 273 follows the movement of the base time point which changes its position with the changes of the threshold. Upon selections of digit numbers indicative of an off-set time in the "Off-set" text frame, and of an averaging time in the "Time" text frame, slider cursors 274 and 275 are moved to positions corresponding to selected numbers, respectively. Their positions of movement can be clearly confirmed visually by their cursor lines. The movement of slider cursors 274 and 275 is linked with the selection of numbers in the "Off-set" text frame and the "Time" text frame. Therefore, setting of the off-set time and averaging time is enabled also by the movement of the slider cursors.

In step S-10-6, it is set up for the averaging whether to be executed in an automatic mode or in a manual mode (S-10-7). Then, when "Set-up OK" button is clicked in step S-10-8, addition is executed. When "Cancel" button is clicked, all of the averaging conditions are canceled. As for the addition, a time (t: base time) is searched for a channel at which a wave thereof exceeds its set-up threshold (S-10-9), then its waveform is displayed with time (t) in the center thereof, that is, the waveform in a time slit between t−50 ms and t+50 ms is displayed with time (t) positioned at the center of the display (S-10-10), then it is judged whether the manual mode cancel is selected or not (S-10-11), if not, addition of its waveforms is executed (S-10-12). Steps from S-10-9 to S-10-12 are repeated as many as the counts of addition for each channel, and the added data are divided by the counts of addition (S-10-13), then the averaging process is completed.

As described above, on the of the averaging process shown in FIG. 27, various conditions for the averaging process can be input and operated both from the operation region and the analysis data display area 805. Therefore, it can be arranged such that, for example, general conditions are set up roughly on the analysis data display area, and details thereof are set up in the operation region, thereby providing versatile set-up methods to the operator, and minimizing the time required for setting such conditions. Especially, in this embodiment of the invention, any particular channel which is to serve as the reference in the averaging process can be selected from a plurality of channels displayed on the analysis data display area 805 by designating the most appropriate one of them using the cursor, thereby minimizing inadvertent operation and improving the ease-of-operation. In addition, because the threshold cursor and the slider cursors are displayed in the vicinity of the designated channel, visual recognition is facilitated. Still further, because by means of these threshold cursor and the slider cursors disposed in the vicinity of the designated channel, the entry and/or operation of various conditions for the averaging process can be executed, the eye-movement of the operator is reduced substantially, and the layout of the screen can be set up suitable for visual recognition of the waveforms displayed, thereby minimizing inadvertent operation and improving the operativeness. Furthermore, for the economy of the operation, it may be arranged such that these set-up conditions which are updated are saved to be displayed as the subsequent set-up conditions, or stored in memory with a title attached.

Figure 20:
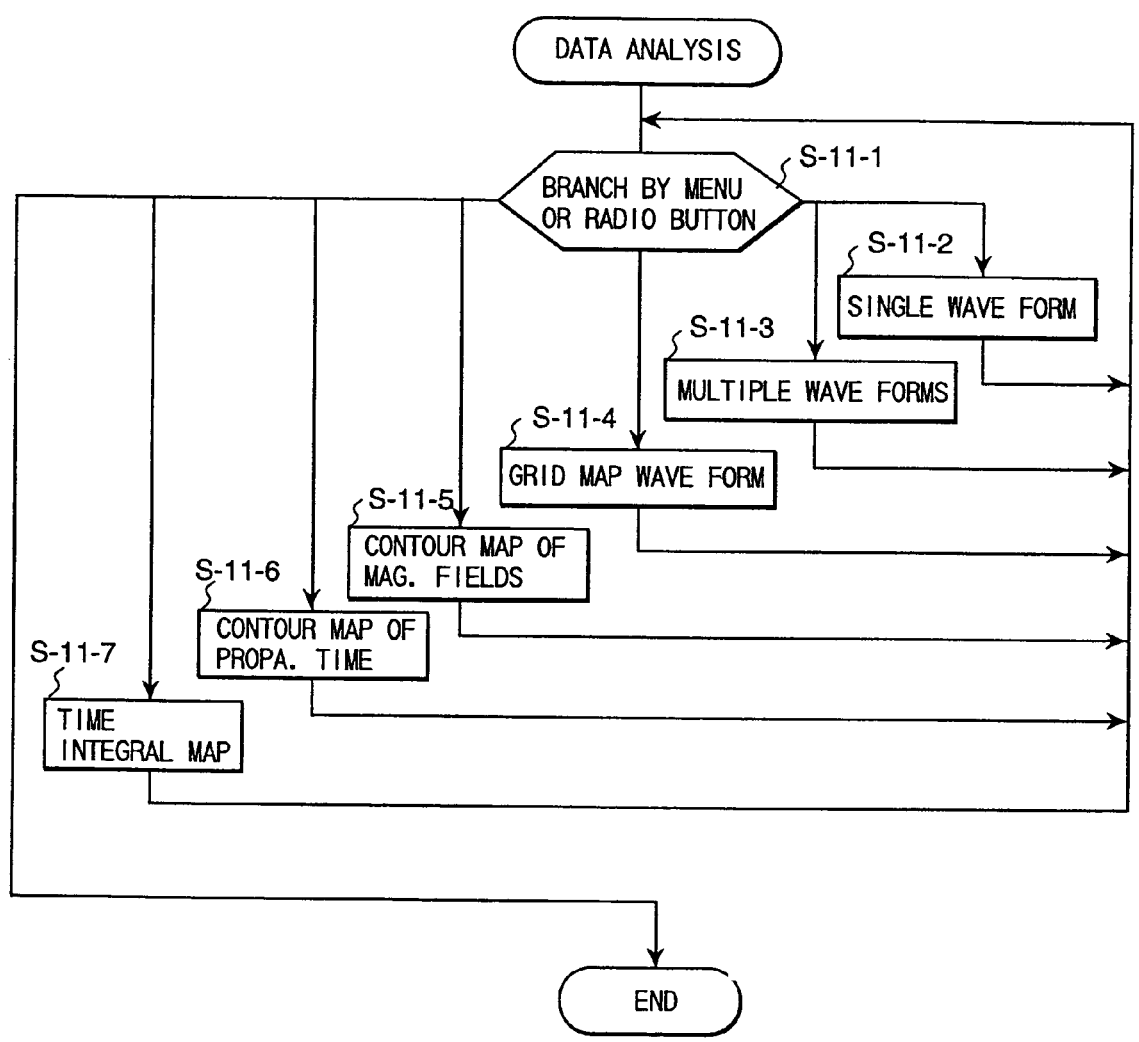
FIG. 20 is a flowchart indicating the flow of data analysis in the data analysis step in FIG. 16.
Figure 28:
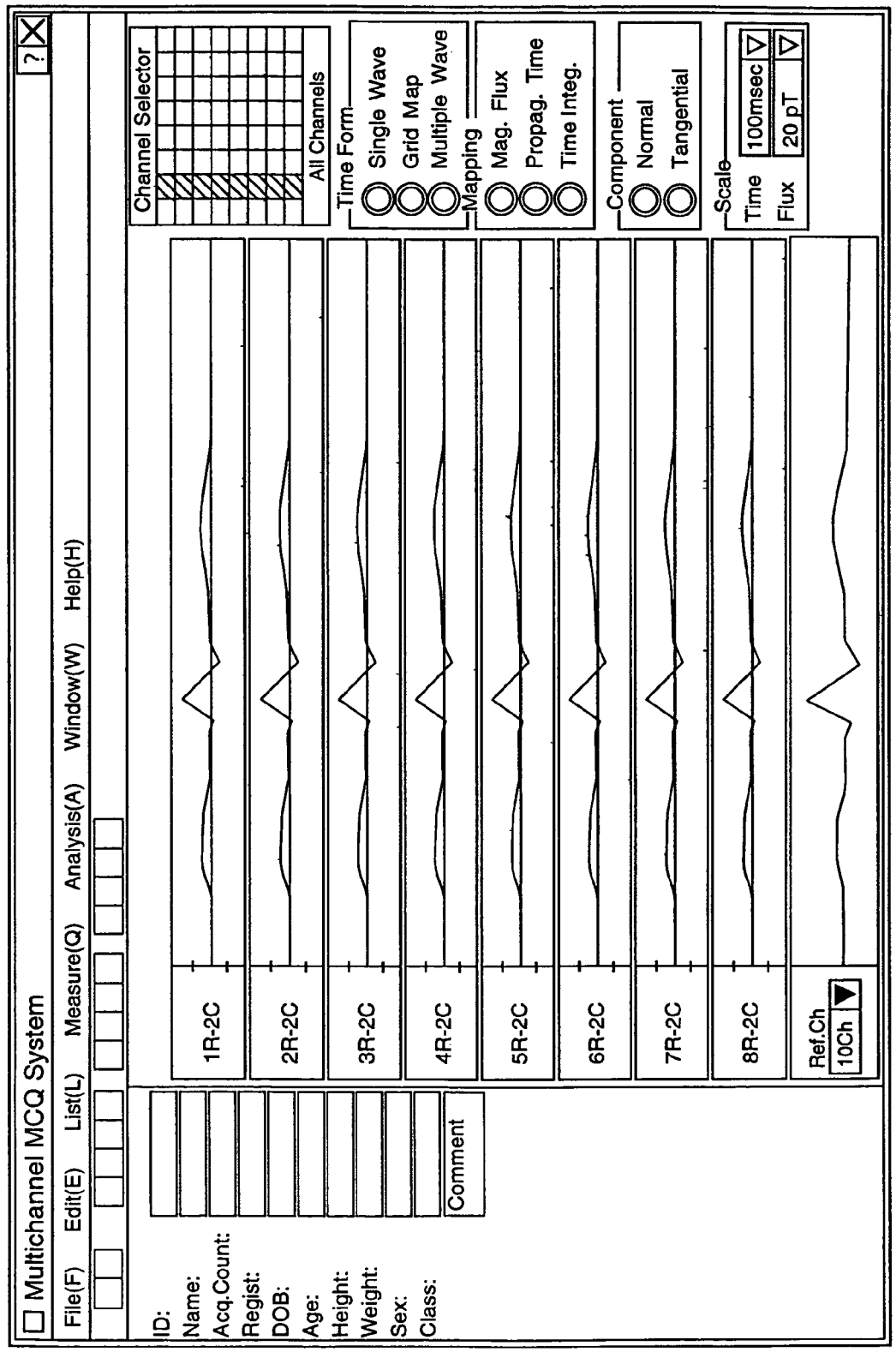
FIG. 28 shows a single waveform screen displayed on the display section of the biomagnetic instrument of FIG. 1.
Figure 29:
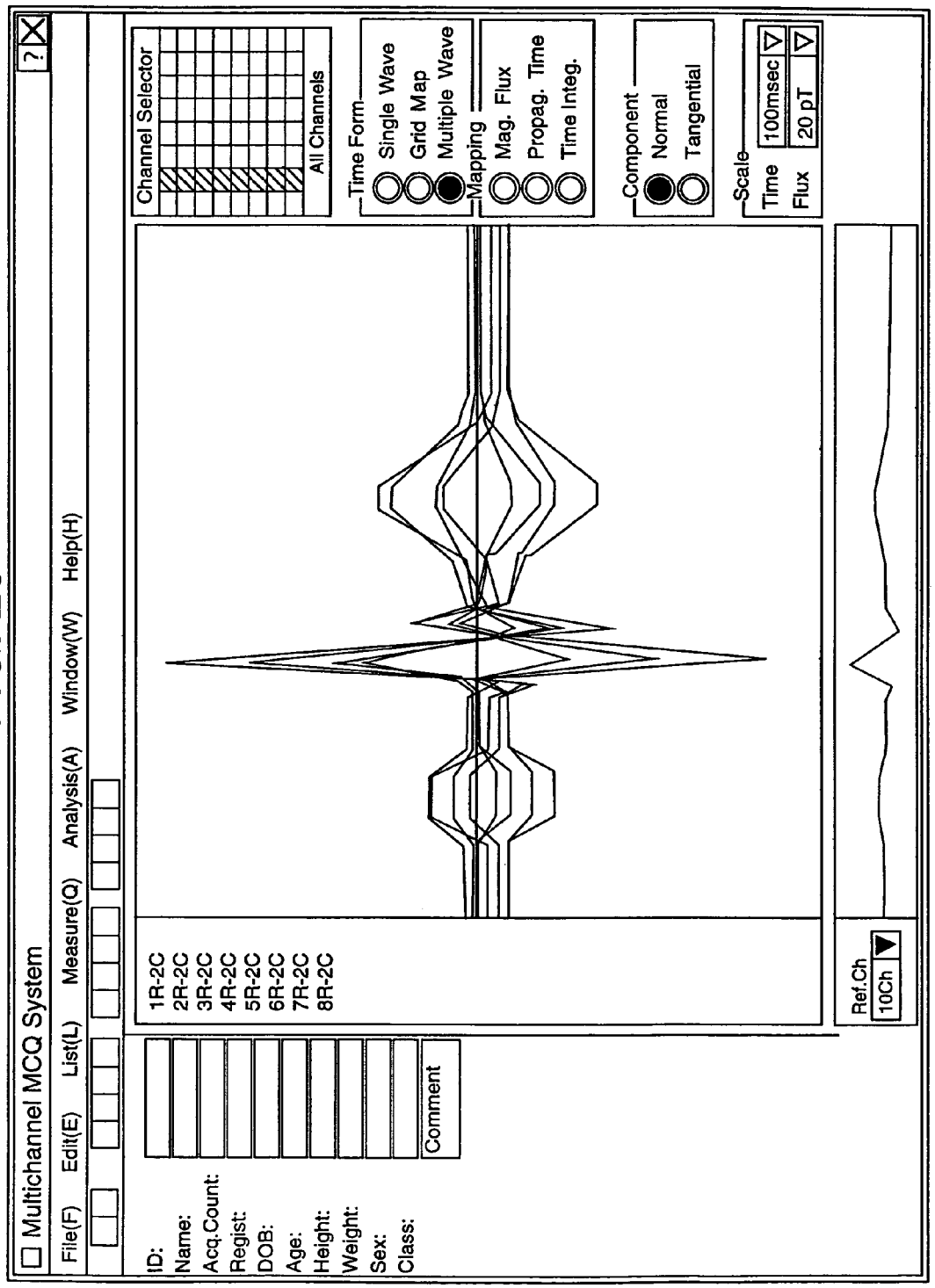
FIG. 29 shows a multichannel wave screen displayed on the display section of the biomagnetic instrument of FIG. 1.
Figure 30:
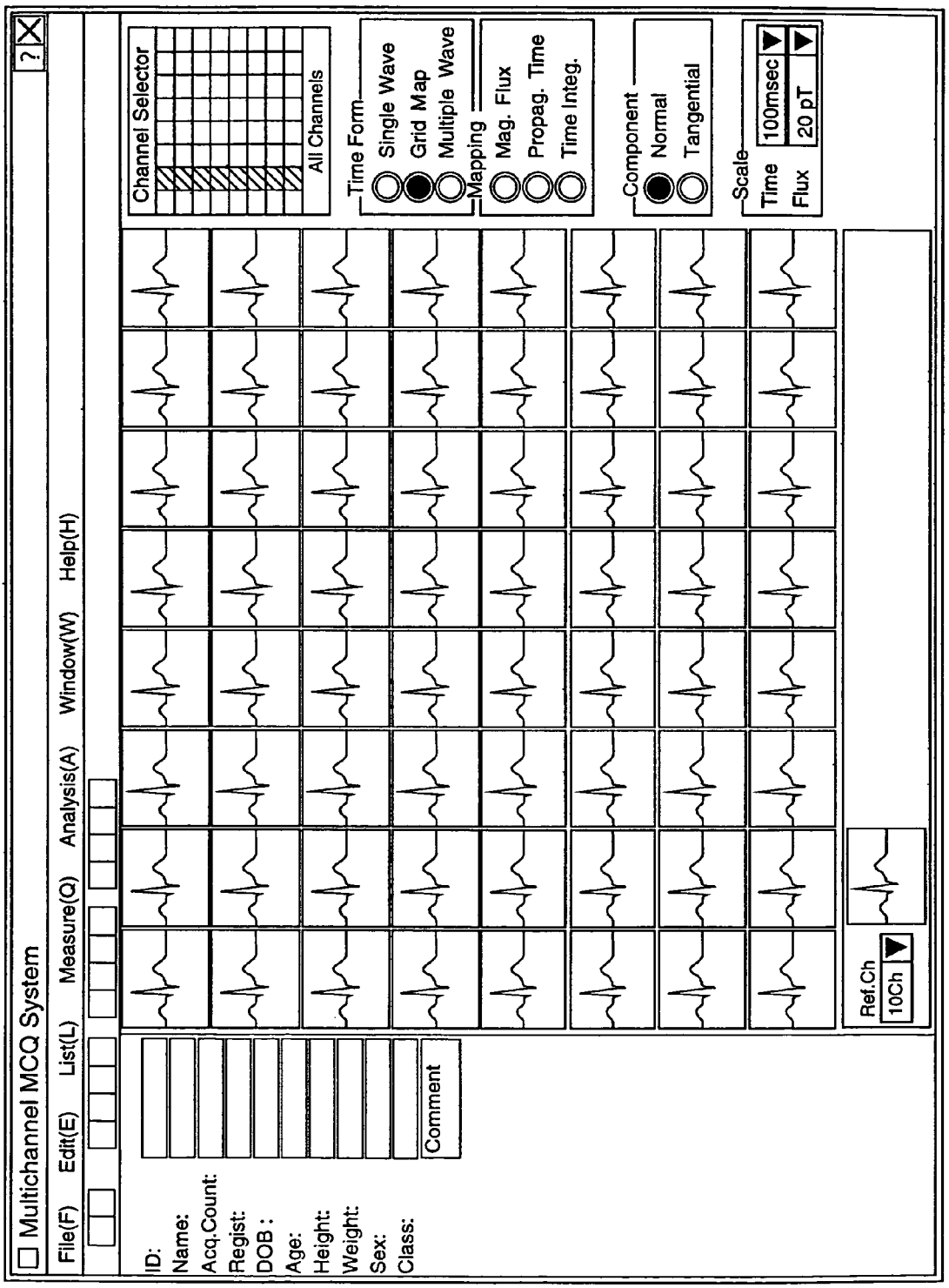
FIG. 30 shows a grid map screen displayed on the display section of the biomagnetic instrument of FIG. 1.
Figure 31:
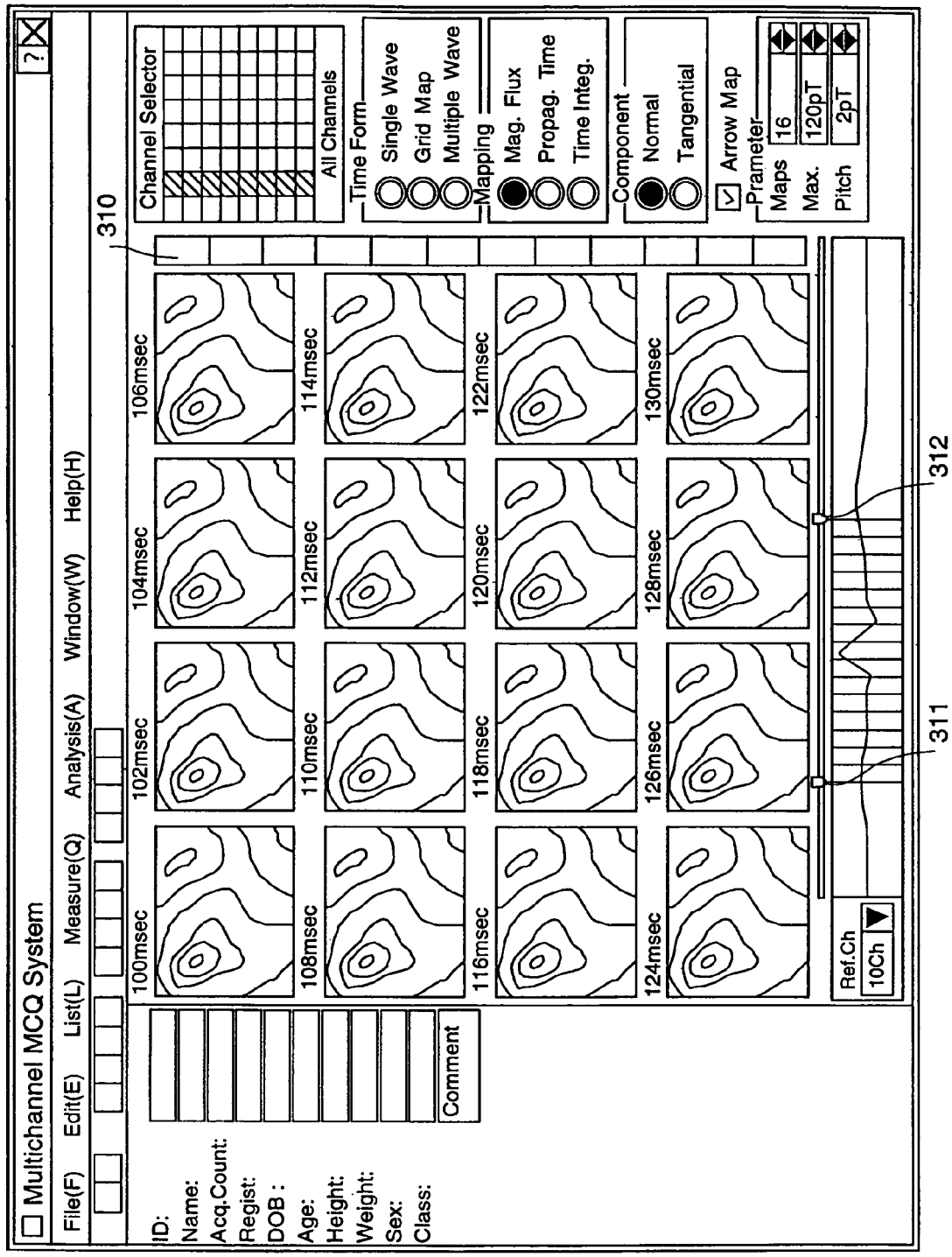
FIG. 31 shows a contour map of magnetic field screen displayed on the display section of the biomagnetic instrument of FIG. 1.
Figure 32:
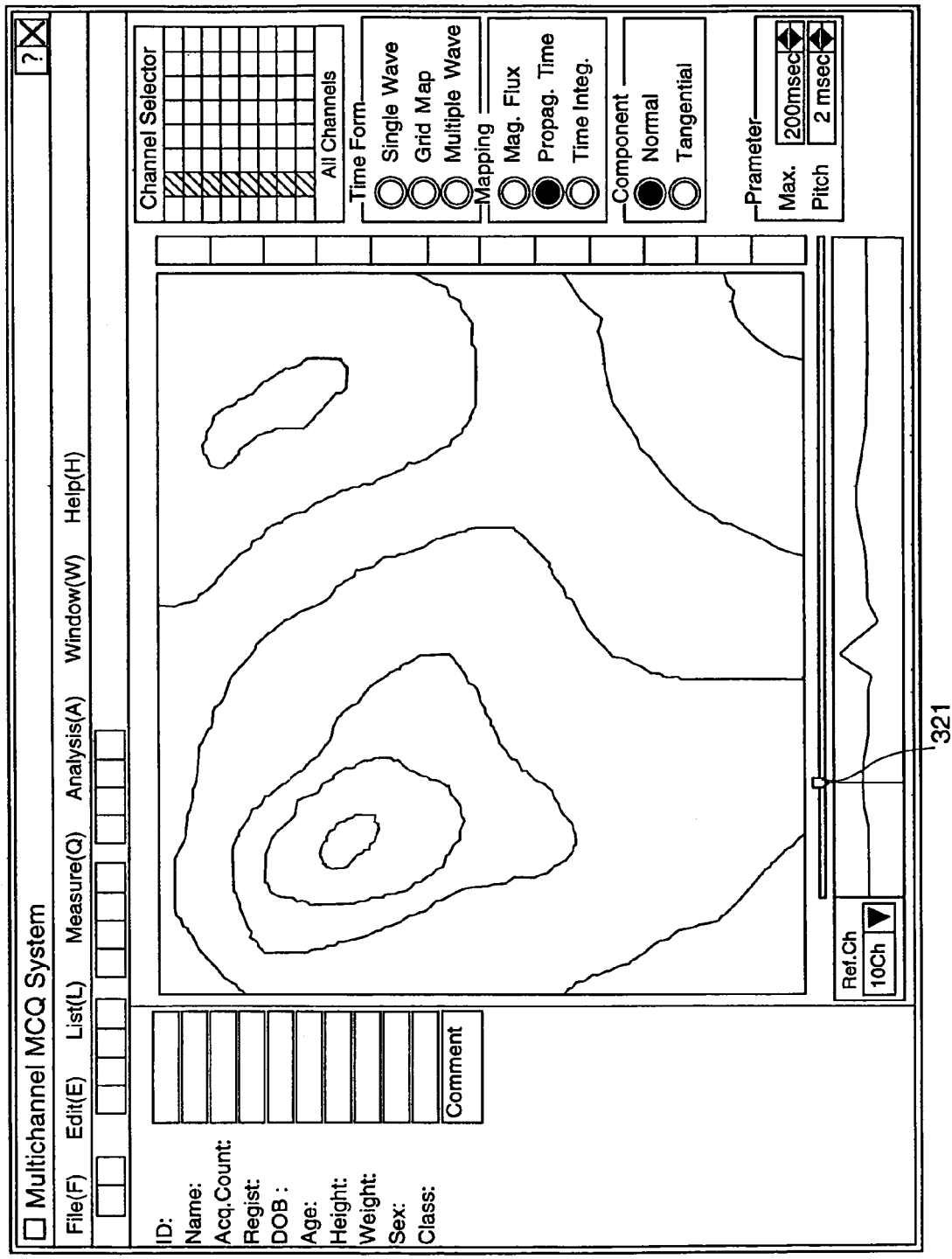
FIG. 32 shows a contour map of propagation time screen displayed on the display section of the biomagnetic instrument of FIG. 1.
Figure 33:
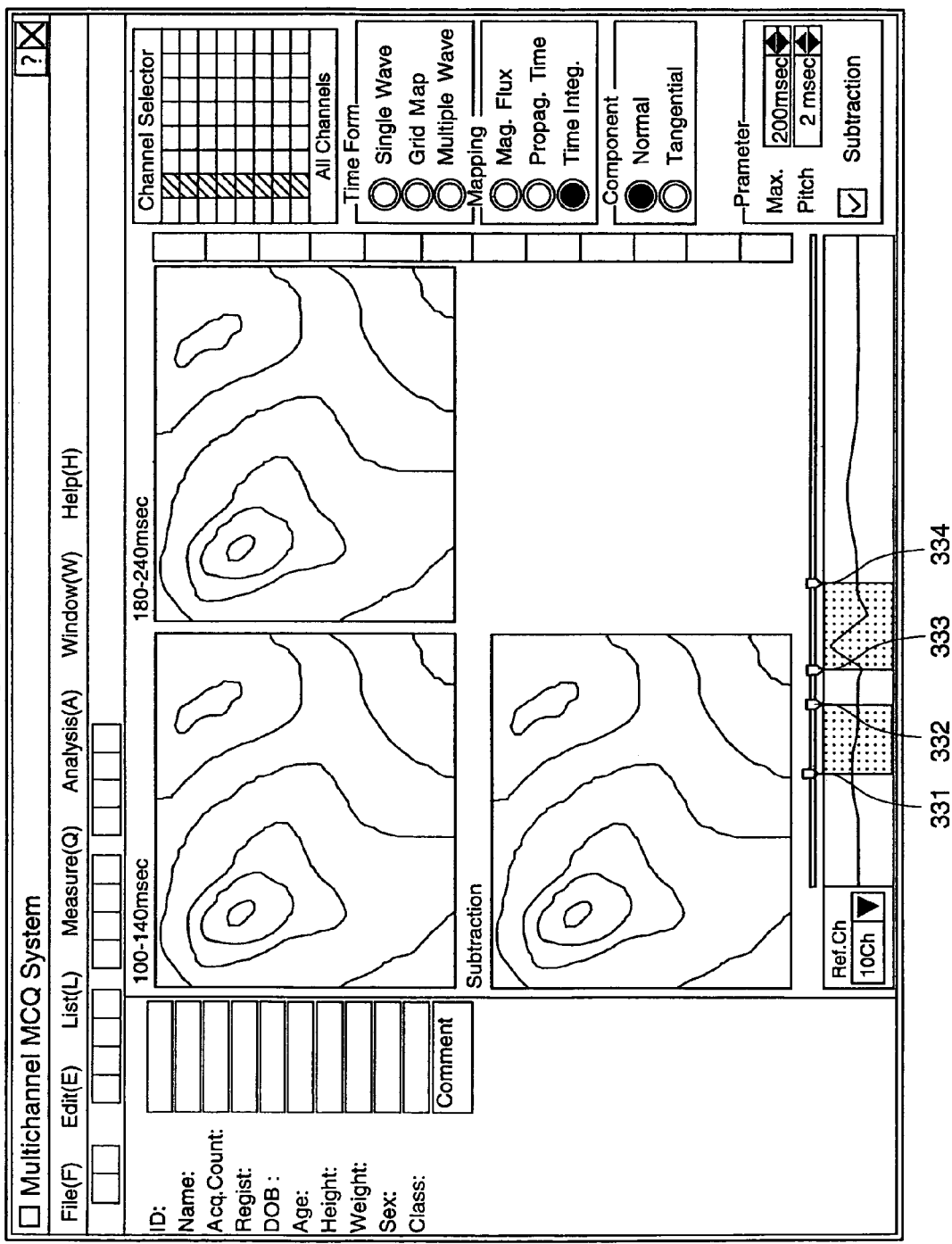
FIG. 33 shows a contour map of time integral screen displayed on the display section of the biomagnetic instrument of FIG. 1.

FIG. 20 shows a flow of the data analysis in step S-11 of FIG. 16. This data analysis is intended for obtaining information necessary for diagnosis of the patient from various waveforms and charts which are displayed. By menu selection in FIG. 9, screens indicative of various types of waveforms and charts can be selectively displayed. Namely, by selecting "Single wave (W)" in "Data Analysis (A)", the single waveform screen of FIG. 28 is displayed (S-11-2); by selecting "Multichannel Waveform (M)" in "Data Analysis (A)", the multichannel waveform screen of FIG. 29 is displayed (S-11-3); by selecting "Grid Map Display (G)" in "Data Analysis (A)", the grid map wave screen of FIG. 30 is displayed (S-11-4); by selecting "Mapping of Magnetic Field (B)" in "Data Analysis (A)", the mapping of magnetic field screen of FIG. 31 is displayed (S-11-5); by selecting "Propagation Time Mapping (P)" in "Data Analysis (A)", the Propagation time mapping screen of FIG. 32 is displayed (S-11-&); and by selecting "Time integral mapping (T)" in "Data Analysis (A)", the time integral mapping screen of FIG. 33 is displayed (S-11-7), respectively. Then, by selecting "Exit the Magnetocardiograph (X)" in "Data Analysis (A)", the system ends.

By clicking a radio button (a circle button) in the operation region, a waveform or chart screen designated by this click operation is displayed alternatively. That is why, in FIG. 20, the branch frame is not tagged with "Branch by Menu", but is tagged with "Branch by Menu or Radio Button". Therefore, according to this embodiment of the invention, various analysis data can be obtained without executing the selection of menus in FIG. 9, but simply clicking the radio button in the operation region, thereby minimizing the operation time and inadvertent operation, as well as improving the operativeness of the system.

A magnetic field strength in "Scale" frame in FIGS. 28–30 indicates a full scale value in unit of pT on the plus side or the minus side relative to a zero level of reference. This full scale value can be selected in its pull-down menu which is opened by clicking a triangle button in its text frame. By clicking a radio frame in "Display Component" frame in FIGS. 28–33, waveforms of a normal component or tangential component can be displayed selectively.

In FIG. 28, waveforms of respective channels selected by the channel selection operation are displayed with their offset time adjusted at the left end of the analysis data region. According to this analysis data displayed on the screen, because respective waves of respective channels are arranged vertically, their waveforms and amplitudes of respective channels can be compared easily. In FIG. 29, the respective waveforms arranged vertically in FIG. 28 are displayed in a superimposed multichannel mode thereby allowing comparison of waveforms and their amplitudes at a glance. Further, in FIG. 30, every channel waveforms are displayed on the screen with the off-set time as the base thereof in the same manner as in FIGS. 28 and 29. Therefore, the operator can select any number of channels which is appropriate therefrom as required for the data analysis.

With reference to FIG. 31, a long rectangular frame 310 is arranged vertically to the right side of the analysis data region as a magnetic field strength index frame. This index frame is partitioned into 12 sections painted with different colors or gradations different from each other. This is contemplated for improving visual perceptibility by painting magnetic field strengths in respective island patterns obtained by contour mapping of magnetic flux according to the invention. Namely, assuming that a center position 311 in the center in the vertical direction of the index frame 310 has a magnetic field strength of zero, and that the upper six sections above the center position 311 is defined as a first to sixth sections sequentially from the below thereof, then it may be arranged such that the first section covers a magnetic field strength range from 0 to 2 pT; the second section covers a magnetic field strength range from 2 to 4 pT; the third section covers from 4 to 6 pT; the fourth section covers from 6 to 8 pT; the fifth section covers from 8 to 10 pT; and the sixth section covers from 10 to 12 pT, respectively. As for the other six sections below the center portion, they may be arranged in the same manner as above. However, the upper sections above the center position indicate plus magnetic field strengthes in the positive direction, while the bottom sections below the center position indicate minus magnetic field strengthes in the negative direction. Respective charts of magnetic field mapping of FIG. 31 are displayed in a different color or with a different gradation according to their respective magnetic field strengthes as defined by respective magnetic field strength index sections and their corresponding colors or gradation. By way of example, warm colors may be assigned to the plus magnetic field strengthes, while assigning cold colors to the minus magnetic field strengthes, and assigning yellow color to the center section. Thereby, respective magnetic field strengthes can be recognized by a difference in colors or its gradation, thereby improving visual perceptibility. In addition, according to this embodiment of the invention, because the index frame 310 is provided in the vicinity of the analysis data display area, respective color objects for comparison, that is, painted colors on the map and preset colors in the index frame 310, can be compared easily for confirmation with a least eye movement, thereby allowing for a precise correspondence to be judged between respective levels of magnetic field strengthes in the index frame and actual colors of the mapping. By way of example, in the embodiment of the invention, the index frame 310 is disposed on the right side of the analysis data display area, however, it not limited thereto, and the same may be arranged anywhere in the vicinity of the analysis data display area, for example, in the upper portion, in the bottom portion or on the left side thereof.

Further, in FIG. 31, a "Map Number" in "Reconstruction Parameter" frame indicates the number of the magnetic field maps to be displayed, a "Maximum Value" therein indicates the magnetic field strength on either end of the index frame 310, and a "Pitch" therein indicates a magnetic field strength range of corresponding to a length of each section in the index frame 310. These values can be selected by clicking its triangle button or inverted triangle button in each corresponding text frame.

In the bottom portion of the analysis data display area, there are displayed an electrocardiac waveform of the reference channel, and two cursors 311 and 312 for specifying mapping time. Between these two cursors 311 and 312 for map time specification, there are displayed a plurality divisional lines with a same pitch. The number of the plurality of division lines is identical with the number of the maps selected by the map number selection operation. Respective positions of the two cursors for mapping time specification are movable independently in horizontal directions. When the distance between the two cursors is changed with the movement of these cursors, pitches of the divisional lines change accordingly, with their pitch distance, however, maintained equal between respective lines. It is, however, not limited thereto, and each divisional line may be provided with a cursor so as to allow for its pitch to be set independently. The number of the contour maps of magnetic field displayed in FIG. 31 is 16, and these contour maps are those obtained at a particular period of time designated by the position of the division lines on the electrocardiac waveform, and each contour map is displayed with its mapping time to show when it is drawn.

Thereby, in the same way as described with reference to FIG. 26, the operator can learn at a glance a particular contour map currently being displayed on the analysis data display area coincides with which range (a width between the two cursors) in the analysis time (a width of its electrocardiac waveform), and the range indicated by the contour map coincides with which area in the analysis time, thereby substantially improving visual perceptibility. Further, the range of, the contour map can be moved and set easily by movement of these two cursors using the mouse. Still further, by allowing the pitch between respective division lines to be set freely, an indefinite portion can be divided densely for more precise analysis while the other portions divided sparsely, thereby offering versatile analysis environments to the operator.

Further, when a "Current Direction" check frame in the operating area is clicked to indicate an arrow mark therein, an arrow mark is displayed on the contour map of magnetic field. This contour map with the arrow mark displayed is referred to as the arrow map (not shown). As for this arrow mark, its position indicates the position of its channel (position of the magnetic sensor), its length indicates the strength of its magnetic field, and its direction indicates the direction of a current converted from that of its magnetic field, respectively.

FIG. 32 shows a contour map of propagation time. In this figure, a start position of propagation time (time t1 in FIG. 7) can be changed by moving the position of cursor 321 movable on the reference wave, and this change in the position of cursor 321 can be enabled by dragging the cursor using the mouse.

With reference to FIG. 33, there are displayed two time integral maps and a subtraction map. This "Subtraction" in the time integral mapping can be displayed readily by clicking its check frame to show a check mark. When the "Subtraction" is checked, four cursors 331–334 appear on the reference wave, and further two time integral contour maps are displayed side by side in the upper portion of the display area, and a contour map of subtraction is displayed in the bottom portion of the display area, respectively. These two time integral maps are obtained from values of cardiomagnetic waves which are time integrated in time slits of 100 ms to 140 ms and 180 ms to 240 ms, respectively, which are set using cursors 331 and 332, and 333 and 334 on the reference wave. These time slits can be changed by dragging cursors 331 and 332 as well as cursors 333 and 334 using the mouse. The subtraction map indicates a difference between these two time integral maps. When no check mark appears, as for the cursors, only two cursors, for example, 331 and 332 are displayed, and as for the time integral mapping, only one time integral map is displayed. Of course, the integral time can be changed by changing the positions of the cursors. As described above, according to the embodiment of the invention, by clicking the check frame in the "Subtraction display", two sets of cursors are displayed for prompting the subsequent operation. Therefore, without causing any ambiguity in operation, its operating time can be reduced substantially, and its operability can be increased because the range of its time slits can be readily set by dragging the two sets of cursors using the mouse.

Figure 21:
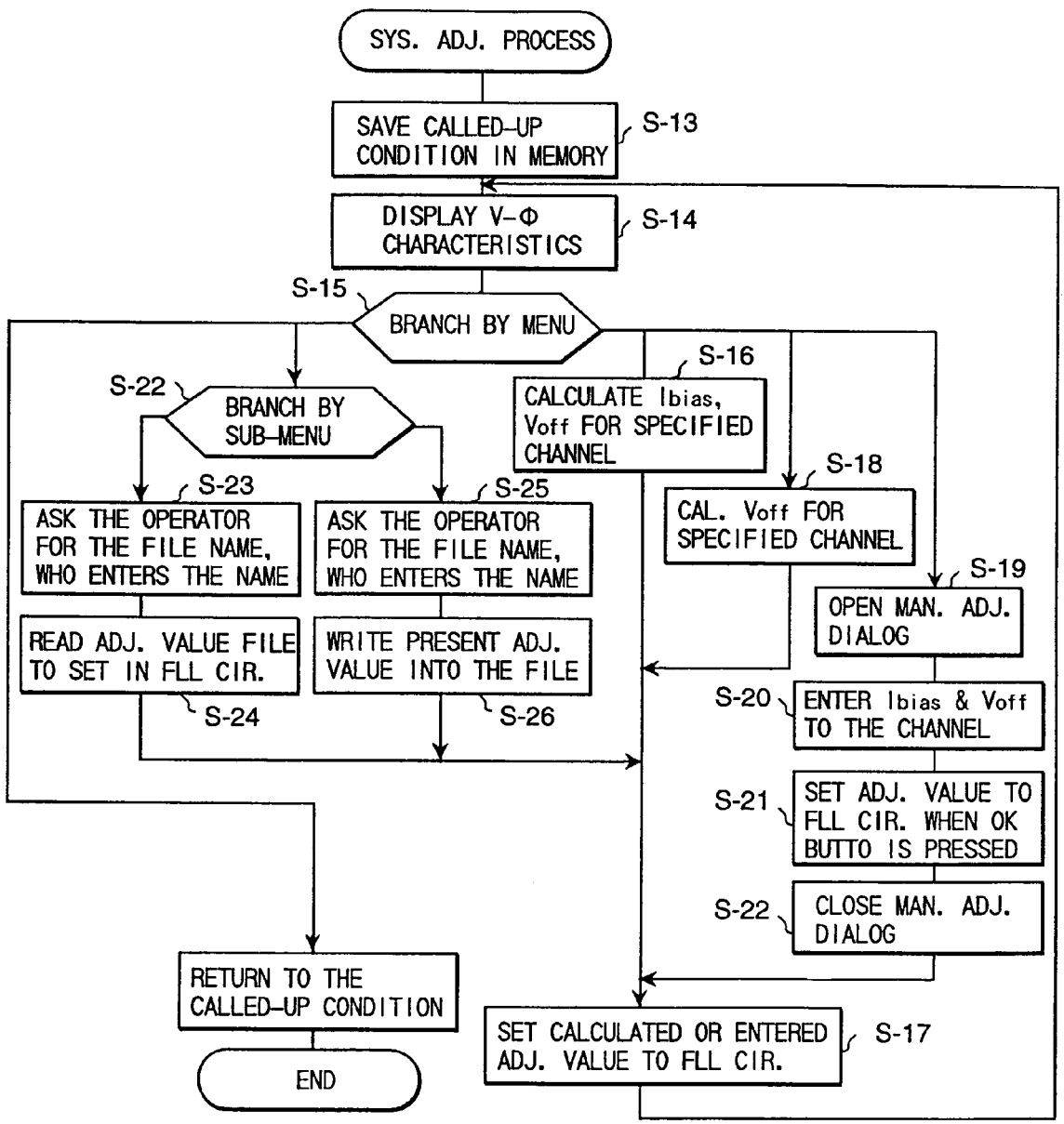
FIG. 21 is a diagram indicating the flow of system adjustment to be executed in the biomagnetic instrument of FIG. 1.
Figure 34:
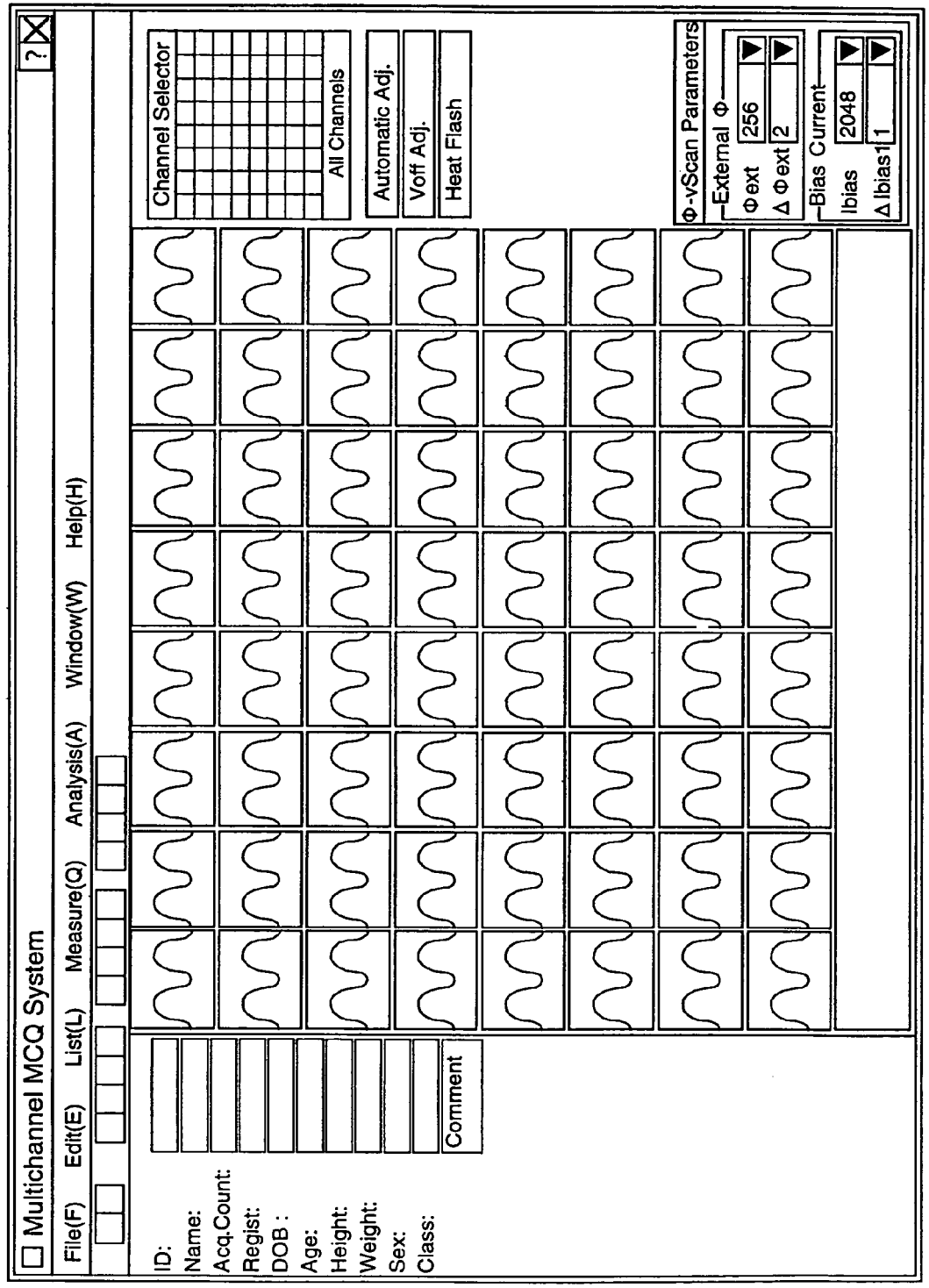
FIG. 34 shows a system adjustment screen displayed on the display section of the biomagnetic instrument of FIG. 1.

FIG. 21 shows the flowchart of the system adjustment according to the invention. The flow is branched to five steps by menu selection in step S-15. In this case, some data currently on display is saved as they are (S-13), and the Φ-V characteristic curve of FIG. 34 is displayed (S-14). In the case where "Full Automatic Adjustment (A)" in "Measurement (Q)" is selected, adjustment values of Ibias and Voff for the all channels are automatically computed (S-16), the automatic computation of which will be described later, and the computed adjustment values are set up in the FLL circuit (S-17), then the flow returns to step S-14.

In the case where "Voff Adjust (V)" of "Measure (Q)" is selected, a value of Voff is computed for the designated channel (S-18), the computation of Voff will be described later, then the flow advances to step S-17 which is already described. In the case where "Manual Adjust. (M)" of "Measure (Q)" is selected, the manual adjustment dialog frame as indicated in FIG. 12 is opened (S-19). When the operator inputs adjustment values of Ibias and Voff for each channel, these input values are accepted (S-20), and they are set in the FLL circuit by clicking "OK" button in the dialog frame(S-21). Then, the dialog frame is closed (S-22), and the flow advances to step S-17.

When the "Adjustment File (F)" of "Measurement(Q)" is selected, the flow is further branched into two substeps by its sub pull-down menu (S-22). Namely, when selection of "Open (O)" in the sub pull-down menu, the operator is asked for its file name, and the operator inputs its file name including the contents of FIG. 11 (S-23). The contents of its adjustment value file are set in the FLL circuit (S-24). Further, by selection either of "Measure (Q)"-"Adjustment Value File (F)"-"Save" and "Alter File Name (A)", the same operation as in step S-23 can be executed (S-25), thereby allowing its adjustment values to be written in the adjustment value file (S-26).

Figure 22:
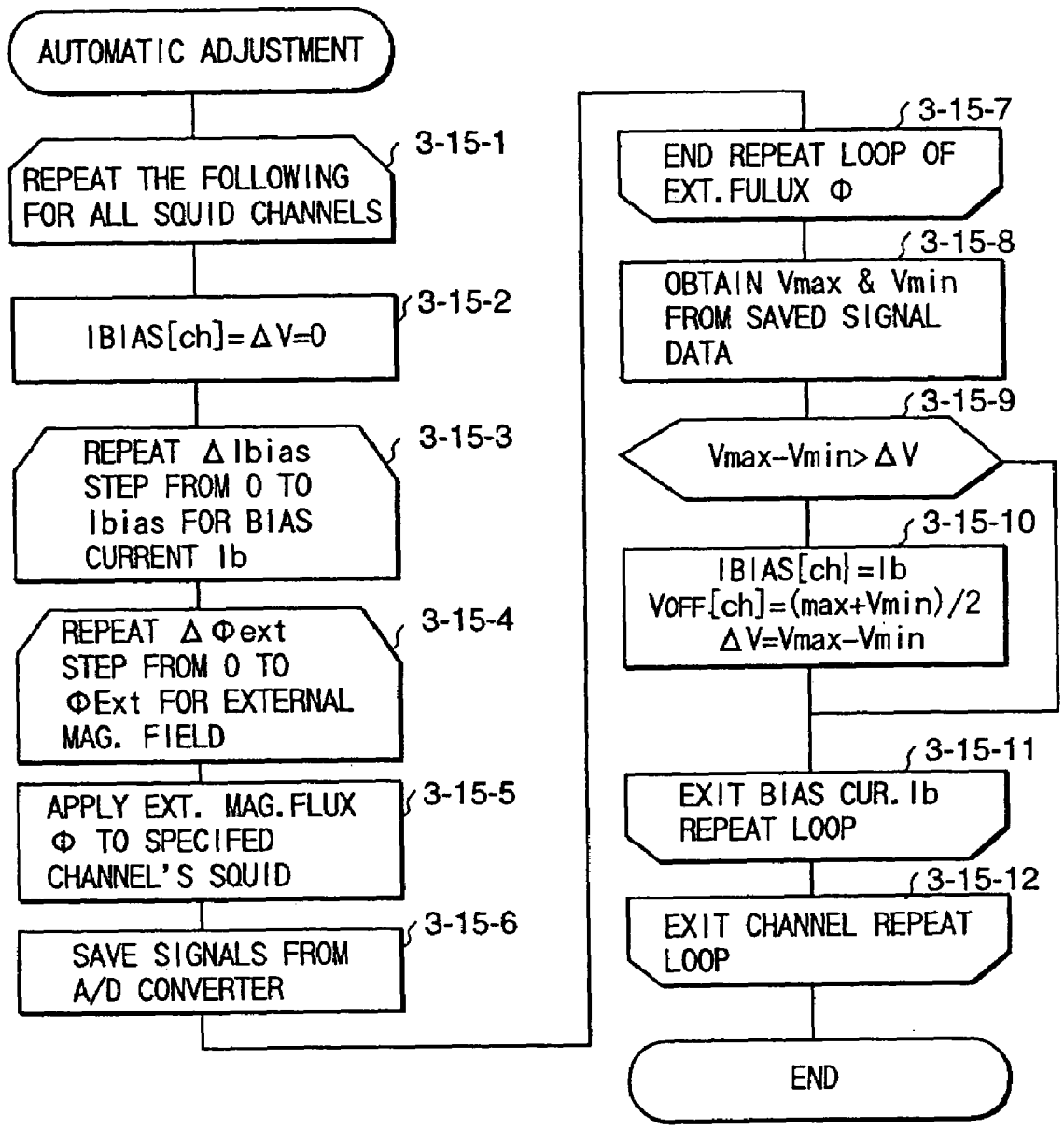
FIG. 22 is a diagram indicating the flow of automatic averaging in the automatic averaging step in the system adjustment flow of FIG. 21.

FIG. 22 shows the flow of the automatic computation in step S-15 in FIG. 21, wherein:

step S-15-1 designates that in case of the full automatic adjustment, the following processes are executed for each one of the whole SQUID channels, and the channel under processing is referred to as "ch";

step S-15-2 designates that the computed bias current and off-set voltage are retained in memories named IBIAS and VOFF, that IBIAS and VOFF can save as many values as the number of the channels, with initial values being zero, and that an amplitude of signals to be saved temporarily of the φ-V characteristic curve is defined as ΔV;

S-15-3 designates that by changing (scanning) bias current Ib from 0 to Ibias, which is designated in "Scan Parameter" frame in FIG. 34, by ΔIbias step for each channel ch, a particular Ibias at which amplitude ΔV of the φ-V characteristic curve becomes maximum is selected as an optimal bias current IBIAS (ch) for the channel ch;

S-15-4 to -8 designate that for bias current between 0 to 1b, amplitude φ of the φ-V characteristic curve is obtained by the following steps: the external magnetic field or magnetic flux φ applied to SQUID of the channel ch is changed (scanned) from 0 to φext which is designated in "Scan Parameter" frame of FIG. 34, by Δφ step, then the signals obtained by A/D conversion are saved, from which its maximum value Vmax and minimum value Vmin are obtained;

S-15-9 to -10 designate that if a difference between maximum value Vmax and minimum value Vmin is larger than ΔV, the value of IBIAS (ch) is replaced by Ibias, the value of VOFF (ch) is replaced by an average of the maximum value Vmax and the minimum value Vmin, and ΔV is replaced by a difference between the maximum value Vmax and the minimum value Vmin, respectively, alternatively, if ΔV is greater than the difference between the maximum value Vmax and the minimum value Vmin, the preceding value is retained.

S-15-11 designates that IBIAS (ch) and VOFF (ch) obtained by repeating the above-mentioned steps of processing until its bias current Ib becomes the Ibias, become the optimal bias current and off-set voltage for SQUID channel ch; and S-15-2 designates that upon execution of the above-mentioned steps of processing to every SQUID channels, the automatic adjustment operation is completed.

Figure 23:
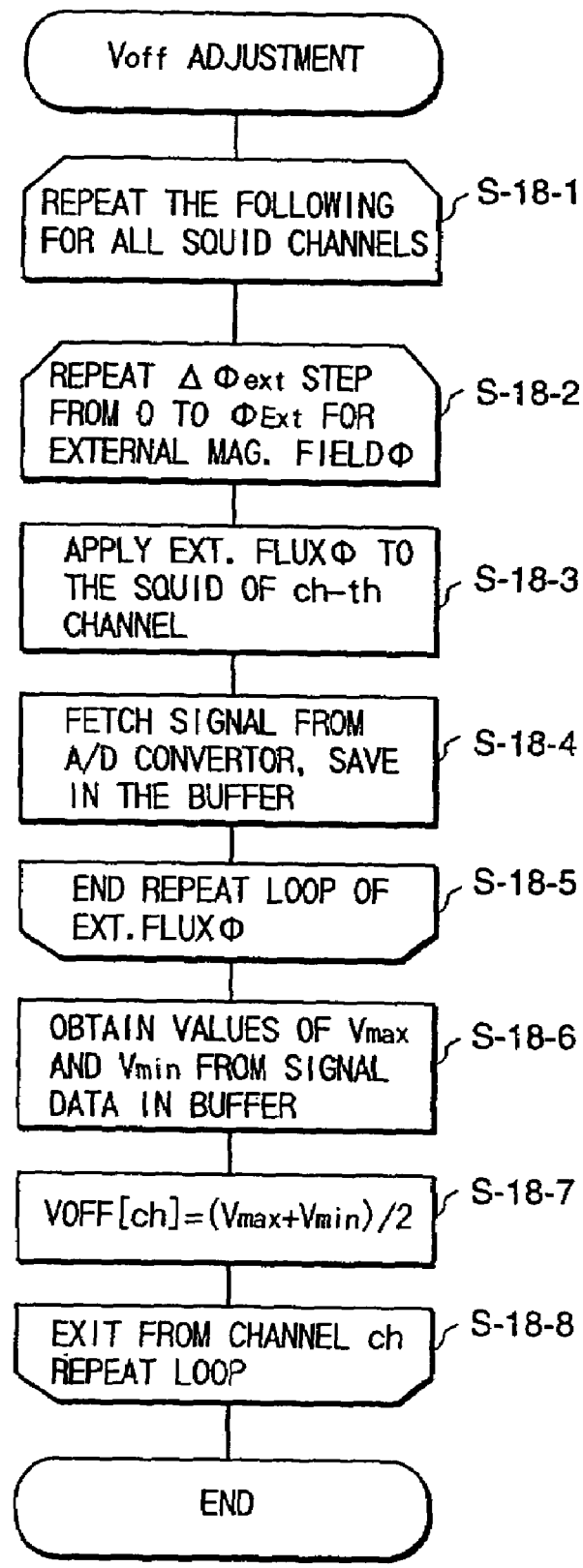
FIG. 23 is a diagram indicating the flow of Voff adjustment in Voff adjustment step in the system adjustment flow of FIG. 21.

FIG. 23 shows the flow of the VOFF adjustment in step 18 of FIG. 21, wherein

S-18-1 designates that in case of the VOFF adjustment, the following steps of processing is executed for each of every SQUID channels;

S-18-2 to -6 designate that by changing (scanning) external magnetic flux φ applied to SQUID of the channel ch from 0 to φext, which is designated in the "Scan Parameter" frame of FIG. 34, by Δφ step, a difference (subtraction) between maximum value Vmax and minimum value Vmin in the signals obtained by A/D conversion are obtained;

S-18-7 designates that an optimal off-set voltage VOFF (ch) for the SQUID channel ch is computed as a difference between the maximum value Vmax and the minimum value Vmin; and S-18-8 designates that upon execution of the above-mentioned steps of processing to the whole SQUID channels, the voff adjustment is completed.

The biomagnetic fields referred to in the description of the embodiments of the invention described hereinabove are magnetic fields produced by myocardial activity in human body, however, it not limited thereto, and any other magnetic fields produced by other activities such as brain and other parts of the body should be included in the scope of the invention.

According to the invention, the method which is easy to operate and control for measuring biomagnetic fields, analyzing the measured biomagnetic field data and displaying the biomagnetic field data in a map as well as the system using the same are provided.

Further, according to the invention, the biomagnetic field data display method and the system using the same are provided which can display the biomagnetic field data on the basis of the magnetic field strengths measured at plurality of measurement positions of the patient in an improved and emphasized manner facilitating visual perception.

According to still further aspect of the invention, because a clear correspondence between each of the plurality of measurement positions of the patient and each channel in the channel matrix is ensured to be identified, measurement and display operations can be executed easily.

According to still more aspect of the invention, because the process function display, the analysis data display and the operating item display are allowed to be displayed on the same, correlated with each other, the contents of display in the analysis data display area can be easily switched simply by selecting a corresponding item in the process function display area and its operating item in the operating region display area while checking by one's own eyes. Further, because the process function display area descriptive of process function items is disposed in the upper portion of the and the patient data display area is disposed in the lower portion thereof, wherein the patient data display area further includes the list data display section which displays information of the patients in a list disposed in the upper portion therein, and the data display section which displays raw data and/or its processed data on the designated patient disposed in the bottom portion therein, the displayed can provide improved visibility and perceptibility.

Still further, because the grid map is displayed as the initial screen, it helps to determine visually whether any of the plurality of measurement positions is faulty, thereby assuring the subsequent measurement operation to be executed safely.

Since it is obvious that may changes and modifications can e made in the above-described details without departing from the nature and spirit of the invention, it is to be understood that the invention is not to be limited to the details described herein.

What is claimed is:

1. A magnetic field map displaying method for detecting a magnetic field generated from a biotest sample by a plurality of magnetic sensors and displaying measurement data obtained on the basis of the detected magnetic field in any desired mode, comprising:
   (1) reading information of biotest samples and measurement data relating thereto from a data storage and displaying on a biotest sample list screen the read-out information of the biotest samples and the read-out measurement data in such a manner as to allow selection thereof;
   (2) on a data measurement screen-setting measurement conditions of a biotest sample selected on the biotest sample list screen and performing an operation for starting measurement; and
   (3) on a data analysis screen, setting analysis conditions of the measurement data relating to the biotest sample selected on the biotest sample list screen and displaying an analyzed result,
   wherein a process function display area for selecting another screen and biotest sample display area for displaying the selected biotest sample information are displayed on each of the biotest sample list screen, the data measurement screen and the data analysis screen in predetermined positions.

2. A magnetic field map displaying method for detecting a magnetic field generated from a biotest sample by a plurality of magnetic sensors and displaying measurement data obtained on the basis of the detected magnetic field in any desired mode, comprising:
   (1) reading information of biotest samples and measurement data relating thereto from a data storage and displaying on a biotest sample list screen the read-out information of the biotest samples and the read-out measurement data in such a manner as to allow selection thereof; and
   (2) on a data measurement screen, setting measurement conditions of a biotest sample selected on the biotest sample list screen, performing an operation for starting measurement, displaying a measurement state under the measurement conditions as a magnetic field waveform, and performing an operation for storing measurement data in the measurement state,
   wherein a process function display area for selecting another screen and a biotest sample display area for displaying the selected biotest sample information are displayed on each of the biotest sample list screen and the data measurement screen in predetermined positions.

* * * * *